US011478727B2

(12) United States Patent
Lauber et al.

(10) Patent No.: US 11,478,727 B2
(45) Date of Patent: Oct. 25, 2022

(54) DIFLUOROACETIC ACID ION PAIRING REAGENT FOR HIGH SENSITIVITY, HIGH RESOLUTION LC-MS OF BIOMOLECULES AND SMALL MOLECULES

(71) Applicant: Waters Technologies Corporation, Milford, MA (US)

(72) Inventors: Matthew A. Lauber, North Smithfield, RI (US); Jennifer M. Nguyen, Uxbridge, MA (US); Ximo Zhang, Framingham, MA (US); Nilini Ranbaduge, Hopkinton, MA (US); Robert Birdsall, Westborough, MA (US); Henry Shion, Hopkinton, MA (US); Melvin Blaze Muttikal Thomas, Stratford, CT (US); Thomas Walter, Ashland, MA (US)

(73) Assignee: Waters Technologies Corporation, Milford, MA (US)

( * ) Notice: Subject to any disclaimer, the term of this patent is extended or adjusted under 35 U.S.C. 154(b) by 201 days.

(21) Appl. No.: 16/848,234

(22) Filed: Apr. 14, 2020

(65) Prior Publication Data

US 2020/0261826 A1 Aug. 20, 2020

Related U.S. Application Data

(63) Continuation-in-part of application No. 16/259,705, filed on Jan. 28, 2019.

(60) Provisional application No. 62/623,059, filed on Jan. 29, 2018.

(51) Int. Cl.
| | | |
|---|---|---|
| *B01D 15/16* | (2006.01) | |
| *B01D 15/30* | (2006.01) | |
| *B01D 15/38* | (2006.01) | |
| *B01D 3/02* | (2006.01) | |
| *G01N 30/72* | (2006.01) | |
| *B01J 20/26* | (2006.01) | |
| *B01J 20/283* | (2006.01) | |
| *B01J 20/22* | (2006.01) | |
| *B01J 20/285* | (2006.01) | |
| *B01J 20/28* | (2006.01) | |
| *C07C 67/54* | (2006.01) | |

(52) U.S. Cl.
CPC ............ *B01D 15/166* (2013.01); *B01D 3/02* (2013.01); *B01D 15/305* (2013.01); *B01D 15/3847* (2013.01); *B01J 20/22* (2013.01); *B01J 20/261* (2013.01); *B01J 20/283* (2013.01); *B01J 20/285* (2013.01); *B01J 20/28052* (2013.01); *C07C 67/54* (2013.01); *G01N 30/7233* (2013.01); *B01J 2220/54* (2013.01)

(58) Field of Classification Search
CPC ...... B01D 15/166; B01D 3/02; B01D 15/305; B01D 15/3847; B01J 20/22; B01J 20/261; B01J 20/28052; B01J 20/283; B01J 20/285; B01J 2220/54; C07C 67/54; G01N 30/7233
See application file for complete search history.

(56) References Cited

U.S. PATENT DOCUMENTS

2015/0316515 A1* 11/2015 Lauber .................. C08F 220/54
73/61.55

OTHER PUBLICATIONS

Yamamoto et al. "Application of partially fluorinated carboxylic acids as ion-pairing reagents in LC/ESI-MS". Taianta, 127, 2014, p. 219-224 (Year: 2014).*
"Catalogo General Reactivos para Analisis y Productos para Quimica Fina 2011/2013 (excerpt)". Panreac. 2013.
"Find the perfect chemicals for your Chromatography applications: Solvents, blends and reagents." Thermo Fisher Scientific. 2015. https://static.fishersci.eu/content/dam/fishersci/en_EU/suppliers/fisherchemical/2_FC_ChromatographyBrochure_EU.pdf.
"Fluorinated Acetic Acids." Kirk-Othmer Encyclopedia of Chemical Technology. 2000. 1-6.
"Guideline on bioanalytical method validation." European Medicines Agency. 2011.
"Hiperpur Hiperpur—Ultra pure reagents for metallic traces analysis." Panreac. Oct. 2004.
Afeyan et al. "Flow-through particles for the high-performance liquid chromatographic separation of biomolecules perfusion chromatography." J. Chromatog. 519(1990): 1-29.
An et al. "A new tool for monoclonal antibody analysis: Application of IdeS proteolysis in IgG domain-specific characterization." mAbs 6.4(2014): 879-893.
Arnold et al. "Workshop Report: Crystal City VI—Bioanalytical Method Validation for Biomarkers." AAPS J. 18.6(2016): 1366-1372.
Banerjee et al. "Electrospray Ionization Mass Spectrometry: A Technique to Access the Information beyond the Molecular Weight of the Analyte." Int. J. Anal. Chem. (2012): 1-40.

(Continued)

*Primary Examiner* — Ryan B Huang
(74) *Attorney, Agent, or Firm* — Womble Bond Dickinson (US) LLP; Deborah M. Vernon

(57) ABSTRACT

The present disclosure relates to the determination of analytes in a sample using chromatography. The present disclosure provides methods of separating an analyte from a sample. A mobile phase is flowed through a chromatography column. The mobile phase includes about 0.005% (v/v) to about 2.50% (v/v) difluoroacetic acid and less than about 100 ppb of any individual impurity, especially metal impurities. A sample including the analyte is injected into the mobile phase. The analyte is separated from the sample.

13 Claims, 22 Drawing Sheets

(56) References Cited

OTHER PUBLICATIONS

Berkowitz et al. "Analytical tools for characterizing biopharmaceuticals and the implications for biosimilars." Nat Rev. Drug Disc. 11(2012): 527-540.

Bioanalytical Method Validation: Guidance for Industry. Biophamaceutics. May 2018.

Bobaly et al. "Challenges in liquid chromatographic characterization of proteins." J. Chromatog. B. 1032(2016): 3-22.

Bobaly et al. "Characterizing various monoclonal antibodies with milder reversed phase chromatography conditions." J. Chromatog. B. 1096(2018): 1-10.

Bobaly et al. "Current possbilities of liquid chromatography for the characterization of antibody-drug conjugates." J. Pharma. Biomed. Anal. 147(2018):493-505.

Bobaly et al. "Influence of acid-induced conformational variability on protein separation in reversed phase high performance liquid chromatography." J. Chromatog. A. 1325(2014): 155-162.

Bobaly et al. "Utility of a high coverage phenyl-bonding and wide-pore superficially porous particle for the analysis of monoclonal antibodies and related products." J. Chromatog. A. 1549(2018): 63-76.

Boyes et al. "High-Resolution Separations for Protein LC/MS." ASMS 2016. Poster 556. http://www.mac-mod.com/pdf/posters-and-presentations/0132-ASMS-Poster_8-18-16.pdf.

Chen et al. "In-depth structural characterization of Kadcyla® (ado-trastuzumab emtansine) and its biosimilar candidate " mAbs. 8.7(2016): 1210-1223.

Chen et al. "Synthesis and optimization of wide pore superficially porous particles by a one-step coating process for separation of proteins and monoclonal antibodies." J. Chromatog. A. 1414(2015): 147-157.

Cheung et al. "Protein folding mediated by solvation: Water explusion and formation of the hydrophobic core occur after the structural collapse." PNAS. 99.2(2002):685-690.

Cohen et al. "Mobile-Phase and Temperature Effects in the Reversed Phase Chromatographic Separation of Proteins." Anal. Biochem. 140(1984): 223-235.

Dodda et al. "Development and validation of bioanalytical liquid chromatography-tandem mass spectrometry method for the estimation of pentoxifylline in human plasma: Application for a comparative pharmacokinetic study." Eur. J. Mass Spectrometry. 2018. (Abstract Only).

Fachi et al. "A systematic and critical review on bioanalytical method validation using the example of simultaneous quantitation of antidiabetic agents in blood." J Chromatog. B. 1055-1056(2017): 61-71.

Fekete et al. "Impact of mobile phase temperature on recovery and stability of monoclonal antibodies using recent reversed-phase stationary phases." J. Sept. Sci. 35(2012): 3113-3123.

Friese et al. "Practical approaches for overcoming challenges in heightened characterization of antibody-drug conjugates with new methodologies and ultrahigh-resolution mass spectrometry." mAbs (2018): 1-11.

Iavarone et al. "Supercharged Protein and Peptide Ions Formed by Electrospray Ionization." Anal. Chem. 73(2001): 1455-1460.

International Search Report and Written Opinion issued in International Patent Application No. PCT/IB2019/050675 dated Jul. 5, 2019.

Kadian et al. "Comparative assessment of bioanalytical method validation guidelines for pharmaceutical industry." J. Pharma. Biomed. Anal. 126(2016): 83-97.

Lippens et al. "Rapid LC-MS Method for Accurate Molecular Weight Determination of Membrane and Hydrophobic Proteins." Anal. Chem. 90.22(2018): 13616-13623.

Mak et al. "Optimizing Mobile Phase Solvent Purity for LCMS." Thermo Fisher Scientific. 2009.

Monroe. "Development of Instrumentation and Applications for Micocolumn Liquid Chromatography Coupled to Time-of-Flight Mass Spectrometry." The University of North Carolina at Chapel Hill. Dissertation, Docotof Philosophy in the Department of Chemistry. 2002.

Schiel et al. "Monoclonal Antibody Therapeutics: The Need for Biopharmaceutical Reference Materials." ACS Symposium Series. 1(2014).

Schuster et al. "Optimized superficially porous particles for protein separations." J. Chromatog. A. 1315(2013): 118-126.

Sharma et al. "Bioanalytical method development and validation of HPLCUV assay for the quantification of SHetA2 in mouse and human plasma: Application to pharmacokinetics study." J. Pharm. Technol. Drug Res. 6(2017): 1-24.

Sochaj et al. "Current methods for the synthesis of homogenous antibody-drug conjugates." Biotechnol. Adv. 33(2015): 775-784.

Tweeten et al. "Reversed-Phase Chromatography of Proteins on Resin-Based Wide-Pore Packings." J. Chromatog. 359(1986): 111-119.

Van Deemter et al. "Longitudinal diffusion and resistance to mass transfer as causes of nonideality in chromatography." Chem. Eng. Sci. 5(1956): 271-289.

Wagh et al. "Challenges and new frontiers in analytical characterization of antibody-drug conjugates." mAbs. (2017):1-22.

Wagner et al. "Superficially porous silica particles with wide pores for biomacromolecular separations." J. Chromatog. A. 1264(2012): 22-30.

Wagner et al. "Tools to Improve Protein Separations." LCGC North America. 33.11(2015): 856-865.

Yamamoto et al. "Applications of partially-fluorinated carboxylic acids as ion-pairing reagents in LC/ESI-MS." Taianta. 127(2014): 219-224.

Yan et al. "Analysis of human antibody IgG2 domains by reversed-phase liquid chromatography and mass spectrometry." J. Chromatog. B. 877(2009): 1613-1620.

You et al. "High-Sensitivity TFA-free LC-MS for Profiling Histones." Proteomics. 11.16(2011): 3326-3334.

Zhang et al. "Development of a rapid RP-UHPLC-MS method for analysis of modificatrions in therapeutic monoclonal antibodies." J. Chromatog. B. 1032(2016): 172-181.

Altmaier et al. "Yes. Increasing LC-MS Sensitivity can be that Simple." Chromatography Today, Buyer's Guide. (2018):58-62.

Bell et al. "Current State of Superficially Porous Particle Technology in Liquid Chromatography." LCGC North America. 33.6(2015): 386-395.

Kirkland et al. "Tools to Improve Protein Separations." LCGC North America. 33.11(2015): 856-865.

Zhou et al. "Chromatographic efficiency and selectivity in top-down proteomics of histones." J.Chromatogr. B. 1044-1045(2017): 47-53.

\* cited by examiner

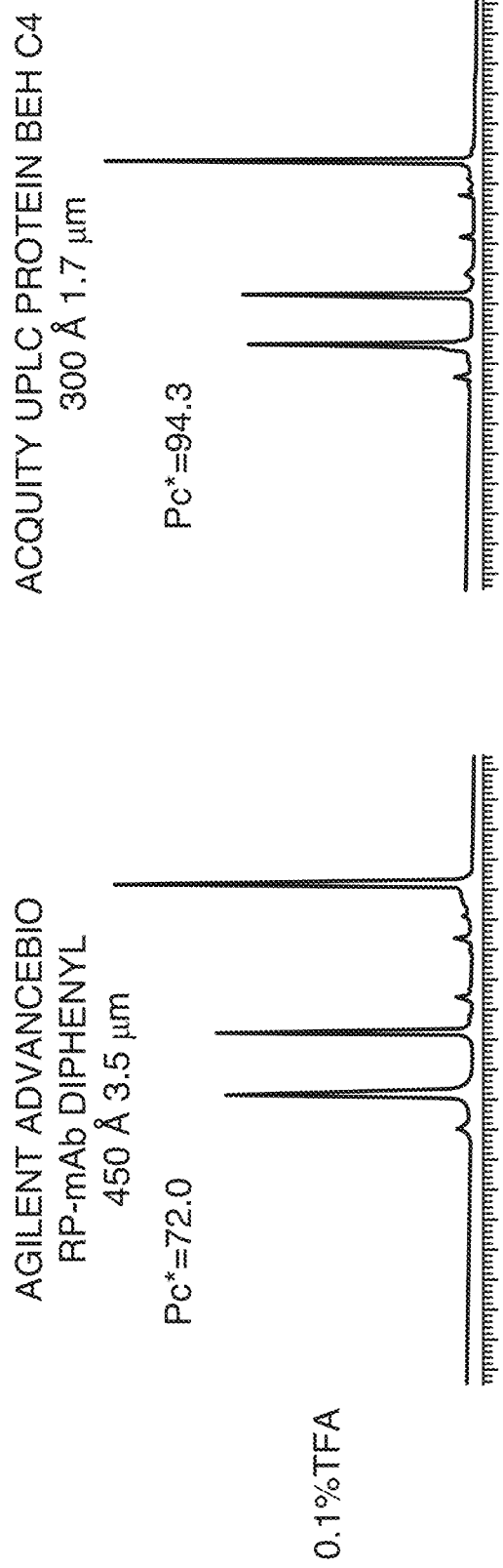
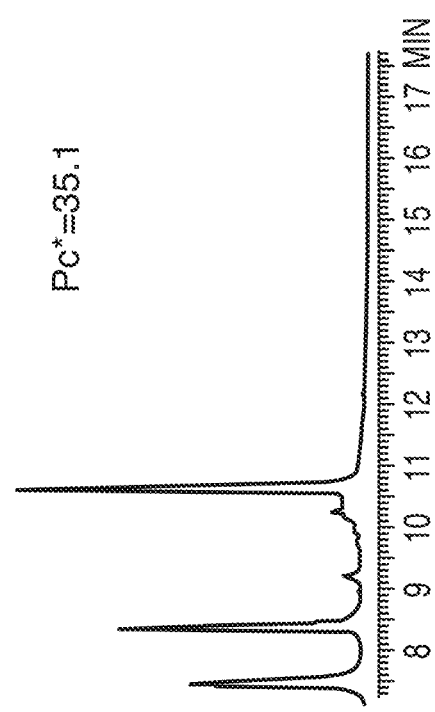
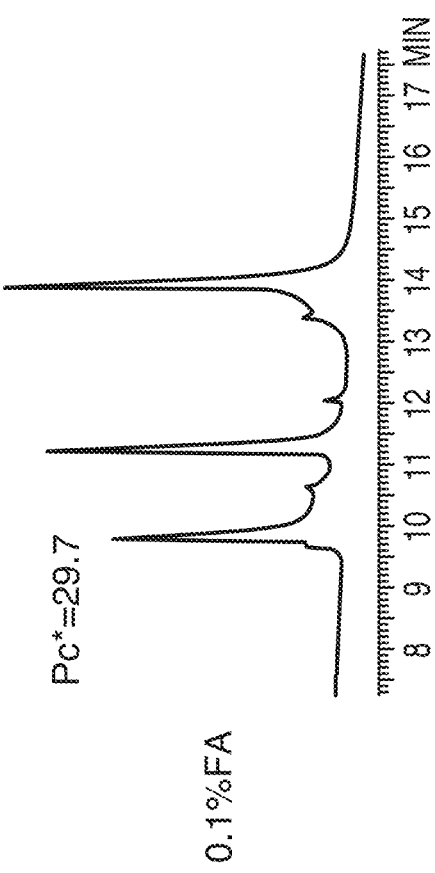

AGILENT ADVANCEBIO
RP-mAb DIPHENYL
450 Å 3.5 μm

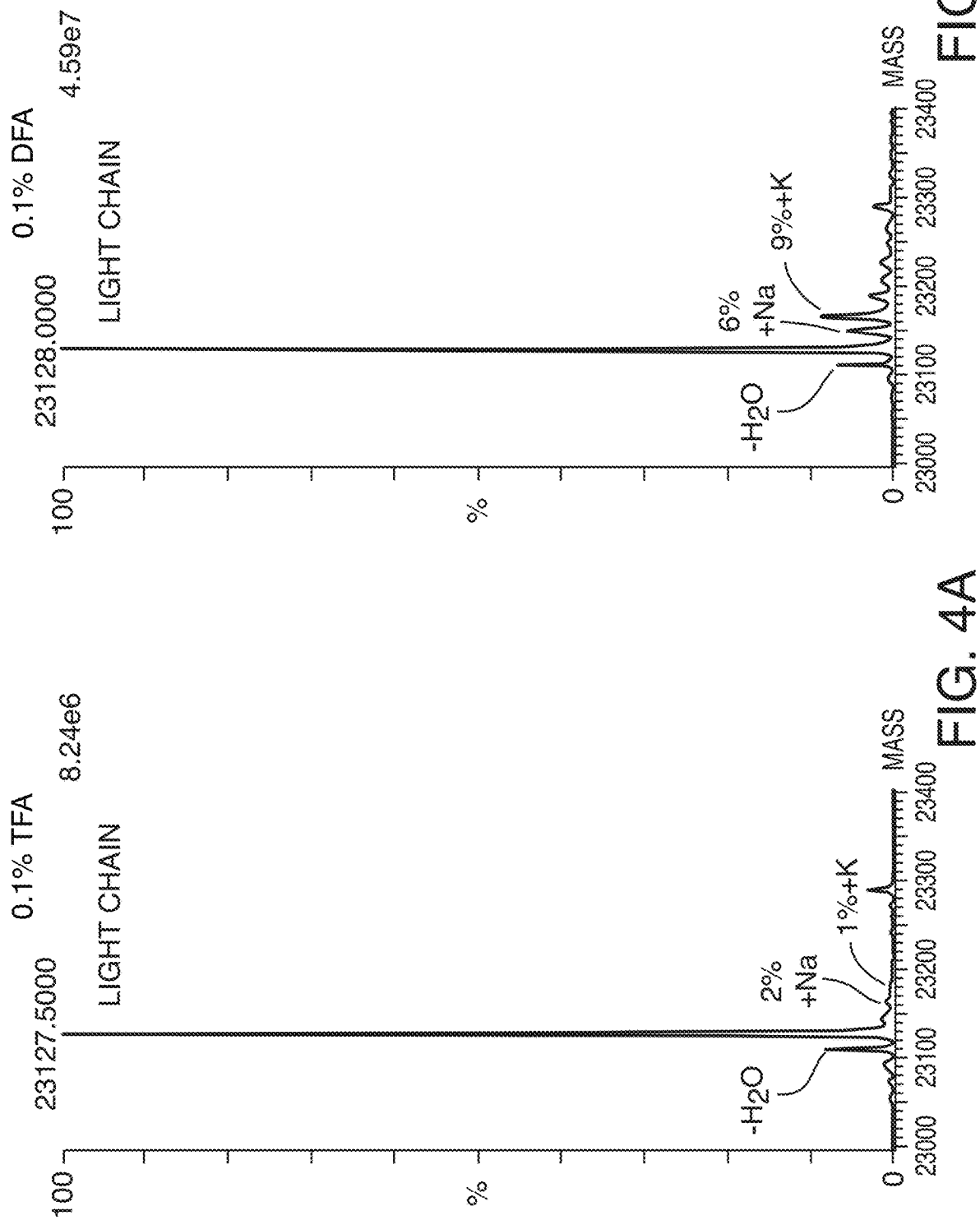

| Ag <10 | Al 480 | As <20 | Au <1 | B <100 | Ba 5 | Be <1 | Bi <1 |
|---|---|---|---|---|---|---|---|
| C N.D. | Ca 2366 | Cd <1 | Ce <1 | Co <1 | Cr 3 | Cs N.D. | Cu 16 |
| Dy <10 | Er <1 | Eu <1 | Fe 275 | Ga <1 | Gd <1 | Ge <1 | Hf <1 |
| Hg <100 | Ho <1 | In N.D. | Ir <1 | K <20 | La <10 | Li <10 | Lu <1 |
| Mg 130 | Mn 2 | Mo <1 | Na 1500 | Nb <1 | Nd <10 | Ni <10 | Os <1 |
| P N.D. | Pb 2 | Pd <1 | Pr <1 | Pt <10 | Rb N.D. | Pe <1 | Ph <1 |
| Ru <10 | S N.D. | Sb <1 | Sc 9 | Se <10 | Si N.D. | Sm <1 | Sn 11 |
| Sr 2 | Ta <10 | Tb <1 | Te <1 | Th <10 | Ti <20 | Tl <10 | Tm <1 |
| U <10 | V <10 | W <1 | Y <1 | Yb <10 | Zn 6500 | Zr <10 | |

FIG.5

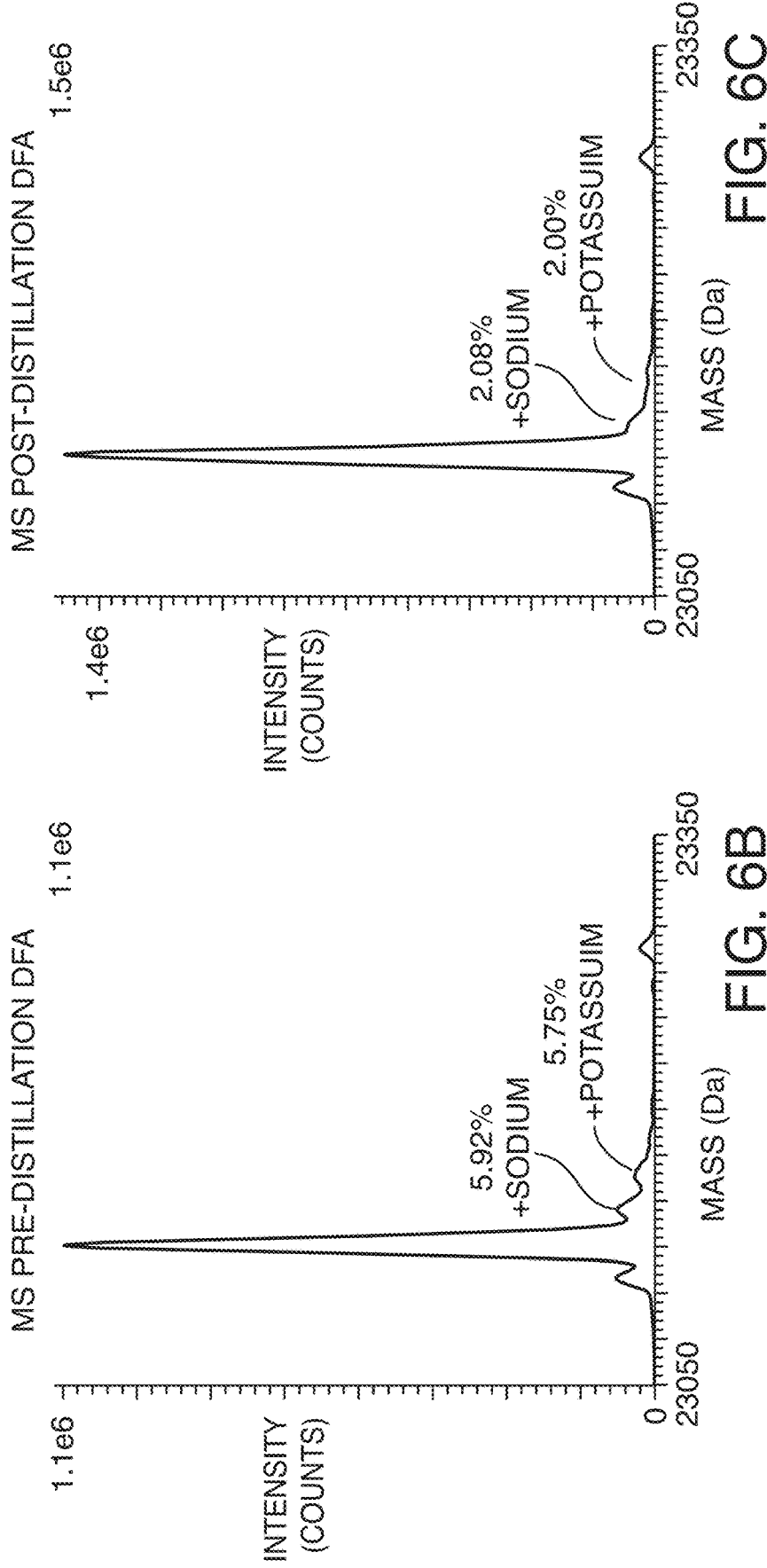

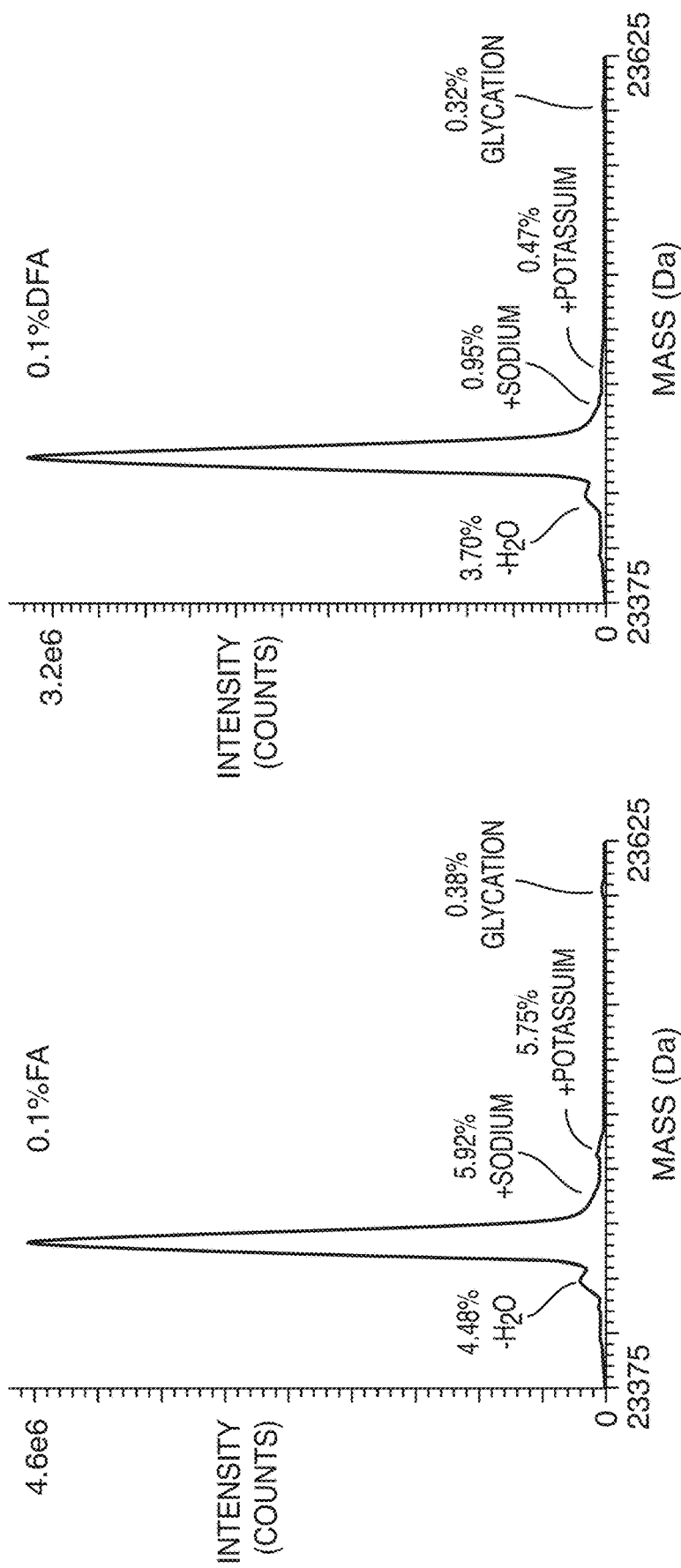

DIFLUOROACETIC ACID ION PAIRING REAGENT FOR HIGH SENSITIVITY, HIGH RESOLUTION LC-MS OF BIOMOLECULES AND SMALL MOLECULES

CROSS-REFERENCE TO RELATED APPLICATIONS

This application is a continuation-in-part of U.S. utility patent application Ser. No. 16/259,709 filed on Jan. 28, 2019, entitled "Difluoroacetic Acid Ion Pairing Reagent for High Sensitivity, High Resolution LC-MS of Biomolecules," which claims priority to U.S. provisional patent application No. 62/623,059 filed on Jan. 29, 2018, entitled "Difluoroacetic Acid Ion Pairing Reagent for High Sensitivity, High Resolution LC-MS of Proteins," the entire contents of which is hereby incorporated herein by reference.

FIELD OF THE TECHNOLOGY

The present disclosure relates to methods of separating an analyte from a sample. More particularly, the present disclosure relates to the use of high purity difluoroacetic acid as a mobile phase in high resolution liquid chromatography-mass spectrometry to separate and detect an analyte from a sample.

BACKGROUND

Mass spectrometry ("MS") is an analytical technique that measures the mass-to-charge ratio of a charged molecule or molecule fragments formed from a sample. MS is used to analyze the mass, chemical composition, and/or chemical structure of a sample of interest. In general, MS includes three steps: ionizing a sample to form charged molecules or molecule fragments (i.e., ions); separating the ions according to their mass-to-charge ratio; and detecting the separated ions to form a mass-to-charge signal (i.e., spectra). The formation of the ions can be achieved through routine MS ionization techniques, such as, for example, Electrospray ionization (ESI), Fast Atom Bombardment (FAB), Chemical Ionization (CI), Electron Impact (EI), Atmospheric Solids Analysis Ionization (ASAI), Atmospheric Pressure Photoionization (APPI), Desorption Electrospray Ionization (DESI), Atmospheric Pressure Vapor Source (APVS), or Matrix-Assisted Laser Desorption/Ionization (MALDI).

There are many different types of MS devices. For example, sector, time-of-flight, quadrupole, ion trap, Fourier transform ion cyclotron resonance, and tandem (two or more of the above combined in tandem or orthogonal) mass spectrometers are all different instruments that are considered to be MS devices. Certain characteristics of MS analysis include, e.g., mass accuracy, resolution, sensitivity, dynamic range, selectivity, and specificity, etc.

Protein reversed phase liquid chromatography ("RPLC") is heavily dependent on the conditions under which it is performed. The best resolving power has, to date, only been achieved through the use of ion pairing with a hydrophobic, acidic mobile phase additive, like trifluoroacetic acid ("TFA"). However, TFA is known to suppress electrospray ionization mass spectrometry signals and to complicate MS spectra with interference due to its ability to form gas-phase ion pairs with positively-charged analyte ions. Consequently, a weaker ion pairing additive, formic acid, has been preferred by some. However, with formic acid mobile phases, protein RPLC methods fail to approach their optimal resolving power.

Several alternative mobile phase additives have been proposed over the years. In 2002, Monroe and co-workers proposed the use of monofluoroacetic acid for peptide LC-MS, showing that it could afford slightly better chromatography than formic acid and better ion yields versus TFA. Monroe, M. E., *Development of Instrumentation and Applications for Microcolumn Liquid Chromatography Coupled to Time-of-Flight Mass Spectrometry*, The University of North Carolina at Chapel Hill, 2002. Serious concerns were, however, raised over the use of any monohalogenated acids given their acute toxicity and ability to disrupt the citric acid cycle. In pursuit of another viable alternative acid modifier, Monroe and co-workers considered the use of DFA, but failed to pursue additional work. Id.

Yamamoto et al. explored the use of DFA for the reversed phase separation and MS detection of small molecule, basic analytes, such as imipramine and nadolol. Yamamoto, E. et al., *Application of partially fluorinated carboxylic acids as ion pairing reagents in LC/ESI-MS*, Talanta 2014, 127, 219-24. The analysis demonstrated that DFA is nearly as effective as TFA in increasing chromatographic retention of analytes but that it can do so without significant detriment to ionization. Id.

Wagner et al., published on the effects of a one-to-one exchange of TFA for DFA and its resultant use for protein RPLC at a conventional mobile phase modifier concentration of 0.1% (v/v). Wagner, B. M., et al, *Tools to Improve Protein Separations*, LCGC North America, 2017, 33 (11), 856-865. Wagner and co-workers showed that similar chromatographic results could be obtained for an intact monoclonal antibody using either method condition. Id. Wagner suggested, but did not show, that DFA could be a more MS friendly methodology.

SUMMARY

What is needed is a mobile phase additive for use in biomolecule (e.g., proteins, peptides, and/or glycans and more specifically for the characterization of protein therapeutics such as monoclonal antibodies (mAb) and antibody drug conjugates (ADC)) LC-MS that solves the problems associated with the use of TFA, namely that TFA is known to suppress electrospray ionization mass spectrometry signals and complicate mass spectra due to its ability to form gas-phase ion pairs with positively-charged analyte ions, but that also maintains optimal resolving power of the chromatography. The mobile phase additive/modifier should not only achieve high sensitivity detection, but should also provide gains in the resolution of the chromatography. This technology solves the challenge with biomolecule LC-MS analyses that exists in achieving a balanced optimization between high chromatographic resolution, high mass spectrometric sensitivity, and mass spectral quality (namely the lack of undesired ion adducts).

To solve the problems related to the use of TFA in biomolecule (e.g., protein, peptide, and/or glycan) LC-MS (e.g., RPLC), the technology provides methods based on low concentrations of an alternative acid, difluoroacetic acid ("DFA"), used with or without phenyl-based stationary phases that are capable of yielding unforeseen optimization of both chromatographic and mass spectrometric performance. The technology also includes a composition of DFA having low level metal impurities, for example, less than about 100 ppb of any individual metal impurity. The purity of DFA leads to the ability to achieve mass spectrometry (MS) quality sufficient for a DFA based liquid chromatography-mass spectrometry ("LC-MS") method to produce interpretable data. The technology also includes the use of other halogenated acids, for example, dichloroacetic acid or dibromoacetic acid. Monohalogenated acids (e.g., monofluoroacetic acid or monochloroacetic acid) can also be used, but are acutely toxic due to their ability to be metabolized as part of the citric acid cycle.

The use of DFA has not yet become routine in biomolecule LC-MS. Current sources of DFA have been found to contain high sodium and potassium concentrations. These salt adducts do not adversely affect separations, but they do disrupt the interpretability of mass spectra. Thus an LC-MS technique was developed that used purified DFA with an unprecedented balance of chromatographic resolution and MS sensitivity. As shown herein, purified DFA affords higher MS sensitivity than TFA and it provides better chromatographic resolution. These gains in analytical capabilities amount to a new LC-MS platform suitable for subunit-level characterization of mAb-based therapeutics, including even a highly hydrophobic cysteine-linked ADC. Unlike previous methods, this purified DFA based RPLC-MS method shows little to no on-column sample degradation, complete analyte recovery, noteworthy proteoform resolution, and 3-fold higher MS sensitivity, which in sum makes it possible to detect and monitor trace-levels of product-related impurities with higher fidelity.

Small molecules are low molecular weight (less than 900 daltons) organic compounds that may be of biological origin or synthetically produced. Typically, small molecules are on the size scale of a nanometer. Proteins and other biomolecules are much larger, and are made of small molecules (e.g., amino acids, monosaccharides) as their building blocks. To study these analytes, high purity and increased MS sensitivity is needed. The present disclosure provides methods and kits that allow for the separation and analysis of a sample including small molecules. In some embodiments, the DFA is distilled to prepare a highly-purified DFA source. The highly-purified DFA limits the amount of all impurities (i.e., not just metal impurities) to less than about 100 ppb. In certain embodiments, the purification of DFA is performed in a vessel to prevent leaching in of contaminates to the DFA before, during, and after the purification process. In some embodiment, the vessel is made from a fluoropolymer such as, for example, perfluoroalkoxy alkane (PFA) that prevents the leaching of polymer or other contaminates into the DFA. In certain embodiments, distilling equipment includes a reservoir and condenser, both fabricated from PFA. The acid is located in the reservoir and heated to the appropriate sub-boiling temperature. When heated to the desired sub-boiling temperature, high purity acid vapor is produced, which condenses on the PFA vessel (condenser) and runs down the side walls into a collection channel and flows into a collection bottle.

The present disclosure relates to a method of separating an analyte from a sample. The method includes flowing a mobile phase through a chromatography column. The mobile phase includes about 0.005% (v/v) to about 2.50% (v/v) difluoroacetic acid and less than about 100 ppb of any individual impurity, including metal impurities. In some embodiments, the mobile phase includes about 0.05% (v/v) to about 1.5% (v/v) difluoroacetic acid and less than about 100 ppb of any individual impurity. In certain embodiments, the mobile phase includes about 0.07% (v/v) to about 0.9% (v/v) difluoroacetic acid and less than about 100 ppb of any individual impurity. In other embodiments, the mobile phase includes about 0.09% to about 0.3% (v/v) difluoroacetic acid and less than about 100 ppb of any individual impurity. In one embodiment, the mobile phase includes about 0.005% to about 0.20% (v/v) difluoroacetic acid and less than about 100 ppb of any individual metal impurity. A sample including the analyte is injected into the mobile phase. The analyte is separated from the sample. The method can include one or more of the embodiments described herein.

The present disclosure also relates to a method of separating an analyte from a sample. The method includes flowing a mobile phase through a chromatography column. The mobile phase includes about 0.005% (v/v) to about 2.50% (v/v) difluoroacetic acid. In some embodiments, the mobile phase includes 0.005% (v/v) to about 0.2% (v/v) difluoroacetic acid. A sample including the analyte is injected into the mobile phase. The analyte is separated from the sample. The analyte is detected with a mass spectrometer. The mass spectrometer produces a mass spectrum having less than about 5% relative ion intensity corresponding to metal or salt adducts. The method can include one or more of the embodiments described herein.

The chromatography column can be a liquid chromatography column or a reversed phase chromatography column. The chromatography column can be a hydrophilic interaction chromatography ("HILIC") column. The chromatography column can be a mixed mode column or a normal phase column. The stationary phase can be a superficially porous silica, organosilica, or fully porous stationary phase bonded with no or various moieties. In some embodiments, the stationary phase material can be a polymeric polystyrene divinyl benzene surface chemistry.

The mobile phase can have less than about 50 ppb of any individual impurity, including metal impurities. The mobile phase can have less than about 20 ppb of any individual impurity. The mobile phase can have less than about 90 ppb, 80 ppb, 70 ppb, 60 ppb, 50 ppb, 40 ppb, 30 ppb, 20 ppb, or 10 ppb of any individual impurity. Examples of individual metal impurity include, but are not limited to, sodium, potassium, calcium, iron, or combinations thereof.

In some embodiments, the mobile phase can have less than about 50 ppb of any individual impurity (including non-metal impurities). The mobile phase can have less than about 20 ppb of any individual impurity. The mobile phase can have less than about 90 ppb, 80 ppb, 70 ppb, 60 ppb, 50 ppb, 40 ppb, 30 ppb, 20 ppb, or 10 ppb of any individual impurity, including any impurity from a contaminant leached in during the purification process. In some embodiments, the purification process utilizes equipment fabricated from PFA.

The mobile phase can have about 0.005% (v/v) to about 2.5% (v/v) difluoroacetic acid. In certain embodiments, especially ones directed to biomolecules, the mobile phase can include 0.01% (v/v) to about 0.05% (v/v) difluoroacetic acid. In some embodiments, the mobile phase can have about 0.02% (v/v) to about 0.05% (v/v) difluoroacetic acid. The mobile phase can have about 0.01% (v/v) to about 0.02% (v/v) difluoroacetic acid. The mobile phase can also include water, acetonitrile, methanol, propanol, butanol, pentanol, or combinations thereof. Other modifiers, buffers, or additives are also possible. For example, embodiments can include one or more of the following water, ammonium hydroxide (i.e., ammonia), ammonium formate, formic acid, pyridine, trimethylamine, ammonium acetate, acetic acid, ammonium bicarbonate, ammonium carbonate, carbonic acid, 1-Methylpiperidene, trifluoroacetic acid. As the mobile phase can include more than one modifier, buffer, additive, various combination exist, including, but not limited to, pyridine and formic acid, trimethylamine and formic acid, trimethylamine and acetic acid, ammonia and formic acid, and ammonia and acetic acid. In certain embodiments, especially ones directed to small molecules, the mobile phase can include 0.01% (v/v) to about 2.0% (v/v) difluoroacetic acid. In some embodiments, the mobile phase can have about 0.02% (v/v) to about 0.9% (v/v) difluoroacetic acid. The mobile phase can have about 0.05% (v/v) to about 0.3% (v/v) difluoroacetic acid.

The analyte can be a biomolecule. The analyte can be a protein, a peptide, a glycan or a combination thereof. The analyte can include multiple proteins, multiple peptides, multiple glycans or combinations thereof.

The analyte can be a small molecule. The small molecule analyte can be of biological origin (e.g., an amino acid, a nucleotide, etc.) or of synthetic origin (e.g., niflumic acid, 2-holoro-4-nitroaniline, etc.). In some embodiments, the small molecule can be acidic. Examples of acidic small molecules include guanosine-'5-monosphate (G5MP), thymidine-'5-monophosphate (T5MP), and niflumic acid. In some embodiments, the small molecule can be basic. Examples of basic small molecules include 6-dimethylaniline, toluidine, 4-chloro-N methylaniline, 2-choloro-4-nitroaniline, thiamine, and histidine. Some small molecules can be neutral, such as, for example, tryptophan. In some embodiments, neutral small molecules can be weakly acidic or weakly basic.

The method can also include determining the molecular weight of the analyte, e.g. a biomolecule, or small molecule. For example, the method can include determining the molecular weight of the protein, the peptide, the glycan, or combinations thereof.

The method can also include detecting the analyte with a mass spectrometer. Analyte ions can be generated by the mass spectrometer. The analyte ions can be generated by electrospray ionization or desorption electrospray ionization. A mass spectrum of the analyte ions can be acquired.

The present disclosure also relates to a kit. The kit includes a chromatography column having a stationary phase material contained inside the column. The kit also includes an ampoule having a volume of mobile phase additive. The mobile phase additive includes difluoroacetic acid and less than about 100 ppb of any individual metal impurity. The kit also includes instructions. The instructions instruct the user to obtain a sample containing at least one biomolecule (e.g., a protein, a peptide, a glycan or any combination) in a sample matrix, dilute the mobile phase additive with a solvent to obtain about 0.005% (v/v) to about 0.20% (v/v) difluoroacetic acid, flow the sample with the diluted mobile phase through the column to substantially resolve and retain the at least one biomolecule (e.g., a protein, a peptide, a glycan or any combination), and detect the at least one biomolecule using a detector. The kit can include one or more of the embodiments described herein.

The stationary phase material can be a superficially porous silica stationary phase bonded with no or various moieties (e.g., phenyl moieties). The stationary phase can be a fully porous silica stationary phase bonded with no or various moieties (e.g., phenyl moieties). In some embodiments, the stationary phase is an organosilica stationary phase bonded with no or various moieties (e.g., phenyl moieties). The stationary phase material can be a polymeric polystyrene divinyl benzene surface chemistry.

The present disclosure relates to a kit that includes a chromatography column having a stationary phase material contained inside the column and a container having a volume of mobile phase. The mobile phase has about 0.005% (v/v) to about 0.20% (v/v) difluoroacetic acid and less than about 100 ppb of any individual metal impurity. The kit also includes instructions for obtaining a sample containing at least one biomolecule (e.g., a protein, a peptide, a glycan or any combination) in a sample matrix, flowing the sample with the mobile phase through the column to substantially resolve and retain the at least one biomolecule (e.g., a protein, a peptide, a glycan or any combination), and detecting the at least one biomolecule using a detector. The kit can include one or more of the embodiments described herein.

The stationary phase material can be a superficially porous silica stationary phase bonded with phenyl moieties. The stationary phase can be a fully porous silica stationary phase bonded with phenyl moieties. In some embodiments, the stationary phase is an organosilica stationary phase bonded with phenyl moieties. The stationary phase material can be a polymeric polystyrene divinyl benzene surface chemistry.

The present disclosure also relates to a method of purifying difluoroacetic acid containing greater than 100 ppb of an impurity. The impurity can be sodium, potassium, calcium, iron, or combinations thereof. The method includes distilling the difluoroacetic acid to obtain a high-purity difluoroacetic acid containing less than 100 ppb of the impurity. The method can include one or more of the embodiments described herein.

The high-purity difluoroacetic acid can contain less than 50 ppb of the impurity. The high-purity difluoroacetic acid can contain less than 20 ppb of the impurity. In some embodiments, the high-purity difluoroacetic acid can contain less than 40 ppb, less than 30 ppb, or less than 10 ppb of the impurity.

Other kits are also within the scope of the present disclosure. For example, a kit directed for use with small molecules is within the scope of the present disclosure. The kit includes a chromatography column having a stationary phase material contained inside the column. The kit also includes an ampoule having a volume of mobile phase additive. The mobile phase additive includes distilled difluoroacetic acid and less than about 100 ppb of any individual impurity. The kit also includes instructions. The instructions instruct the user to obtain a sample containing at least one small molecule in a sample matrix, dilute the mobile phase additive with a solvent to obtain about 0.005% (v/v) to about 2.5% (v/v) difluoroacetic acid (and in some embodiments, from 0.01% (v/v) to about 0.9% (v/v) difluoracetic acid), flow the sample with the diluted mobile phase through the column to substantially resolve and retain the at least one small molecule, and detect the at least one small molecule using a detector. The kit can include one or more of the embodiments described herein.

The kits can include instructions and consumable featuring various chromatography modes. For example, in some embodiments, HILIC chromatographic mode is called for. In other embodiments, mixed mode chromatography is provided in the kit.

The stationary phase material can be a superficially porous silica, organosilica, or fully porous stationary phase bonded with no or various moieties. In some embodiments, the stationary phase material can be a polymeric polystyrene divinyl benzene surface chemistry.

The present disclosure also relates to a method of purifying difluoroacetic acid containing greater than 100 ppb of an impurity. The impurity can be any impurity. The method includes distilling the difluoroacetic acid to obtain a high-purity difluoroacetic acid containing less than 100 ppb of the impurity. The method can further include distilling the difluoroacetic acid in a PFA vessel (e.g., reservoir, condenser) to prevent the leaching in of contaminates before, during, and/or after the purification process. The method can include one or more of the embodiments described herein.

The high-purity difluoroacetic acid can contain less than 50 ppb of the impurity. The high-purity difluoroacetic acid can contain less than 20 ppb of the impurity. In some embodiments, the high-purity difluoroacetic acid can contain less than 40 ppb, less than 30 ppb, or less than 10 ppb of the impurity.

The present disclosure provides a number of advantages over current systems and methodology. For example, purified DFA provides a more MS-friendly alternative to TFA for biomolecule (e.g., a protein, a peptide, a glycan or any combination) LC-MS. In addition, purified DFA provides gains in the resolution of the chromatography as compared to TFA. Purified DFA is especially promising for increasing retention factors and MS sensitivities for small molecule analytes.

BRIEF DESCRIPTION OF THE DRAWINGS

The technology will be more fully understood from the following detailed description taken in conjunction with the accompanying drawings, in which:

FIG. 1E is a chromatogram for reduced, IdeS digested NIST reference material 8671 as observed using a 2.1×50 mm Agilent AdvanceBio RP-mAb Diphenyl 450 Å 3.5 µm column with 0.1% TFA mobile phase modifier, according to an illustrative embodiment of the technology.

FIG. 1F is a chromatogram for reduced, IdeS digested NIST reference material 8671 as observed using a 2.1×50 mm Agilent AdvanceBio RP-mAb Diphenyl 450 Å 3.5 µm column with 0.1% FA mobile phase modifier, according to an illustrative embodiment of the technology.

FIG. 1G is a chromatogram for reduced, IdeS digested NIST reference material 8671 as observed using a 2.1×50 mm Acquity UPLC Protein BEH C4 300 Å 1.7 µm column with 0.1% TFA mobile phase modifier, according to an illustrative embodiment of the technology.

FIG. 1H is a chromatogram for reduced, IdeS digested NIST reference material 8671 as observed using a 2.1×50 mm Acquity UPLC Protein BEH C4 300 Å 1.7 µm column with 0.1% FA mobile phase modifier, according to an illustrative embodiment of the technology.

FIG. 3A shows the total ion chromatogram (TIC) peak heights resulting from the use of various mobile phase modifiers, according to an illustrative embodiment of the technology.

FIG. 3B shows TIC signal-to-noise resulting from the use of various mobile phase modifiers, according to an illustrative embodiment of the technology.

FIG. 4A is a deconvoluted ESI mass spectra for the light chain subunit of NIST reference material 8671 as observed using 0.1% (v/v) TFA with a mass spectrometer commercially available from Waters Corporation (Milford, Mass.) under the tradename Synapt® G2-Si. The relative intensities of undesirable ion adducts, including Na and K, are reported, according to an illustrative embodiment of the technology.

FIG. 4B is a deconvoluted ESI mass spectra for the light chain subunit of NIST reference material 8671 as observed using 0.1% (v/v) DFA with a mass spectrometer commercially available from Waters Corporation (Milford, Mass.) under the tradename Synapt® G2-Si. The relative intensities of undesirable ion adducts, including Na and K, are reported, according to an illustrative embodiment of the technology.

FIG. 5 is a chart showing metal impurities quantified by inductively coupled plasma (ICP)-MS in a sample of DFA (Oakwood, part number 001231, lot D06N). Concentrations are reported in part per billion ("ppb"), according to an illustrative embodiment of the technology.

FIG. 6A shows the influence of sodium and potassium content on pass spectra quality through ICP-MS quantitation of as-received versus distilled DFA, according to an illustrative embodiment of the technology. Separations performed with a BioResolve RP mAb Polyphenyl 450 Å, 2.7 µm, 2.1×50 mm column using a flow rate of 0.2 mL/min, column temperature of 80° C., and 0.25 µg mass loads.

FIG. 6B is a deconvoluted mass spectrum of the NIST mAb LC subunit obtained using as-received DFA, according to an illustrative embodiment of the technology. Separations performed with a BioResolve RP mAb Polyphenyl 450 Å, 2.7 µm, 2.1×50 mm column using a flow rate of 0.2 mL/min, column temperature of 80° C., and 0.25 µg mass loads.

FIG. 6C is a deconvoluted mass spectrum of the NIST mAb LC subunit obtained using distilled DFA, according to an illustrative embodiment of the technology. Separations performed with a BioResolve RP mAb Polyphenyl 450 Å, 2.7 µm, 2.1×50 mm column using a flow rate of 0.2 mL/min, column temperature of 80° C., and 0.25 µg mass loads.

FIG. 8A is a deconvoluted MS spectra of the unmodified LC fragment from the cysteine-linked auristatin ADC obtained using 0.1% MS-grade FA modified mobile phase, according to an illustrative embodiment of the technology. Separations performed with a BioResolve RP mAb Polyphenyl 450 Å, 2.7 µm, 2.1×150 mm column using a flow rate of 0.6 mL/min, column temperature of 80° C., and 1 µg mass loads.

FIG. 8B is a deconvoluted MS spectra of the unmodified LC fragment from the cysteine-linked auristatin ADC obtained using 0.1% distilled DFA modified mobile phase, according to an illustrative embodiment of the technology. Separations performed with a BioResolve RP mAb Polyphenyl 450 Å, 2.7 µm, 2.1×150 mm column using a flow rate of 0.6 mL/min, column temperature of 80° C., and 1 µg mass loads.

FIG. 10 B is a graph providing MS signal response comparison for various acidic small molecule analytes using additives 0.1% (v/v) formic acid (left bar chart); 0.1% (v/v) highly-purified DFA (center bar chart); and 0.1% (v/v) TFA (right bar chart) in both the aqueous and organic mobile phases under ESI negative ionization mode. The error bars show one standard deviation for triplicate measurements.

FIG. 11 B is a graph providing MS signal response comparison at different aqueous/organic ratios for basic small molecule (4-chloro-N-methylaniline) using additives 0.1% (v/v) formic acid (left bar chart); 0.1% (v/v) highly-purified DFA (center bar chart); and 0.1% (v/v) TFA (right bar chart) in both the aqueous and organic mobile phases under ESI positive ionization mode.

DETAILED DESCRIPTION

Figure 1A:
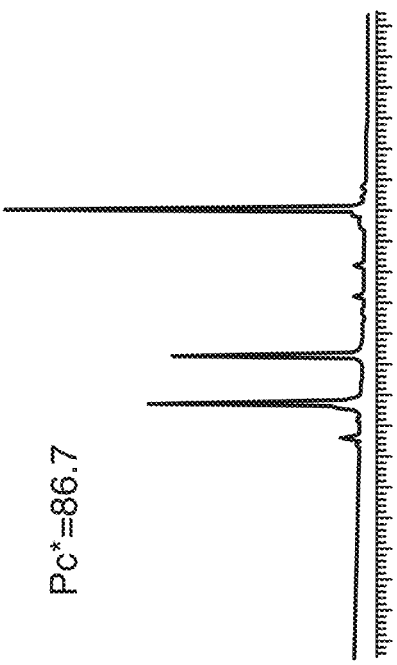
FIG. 1A is a chromatogram for reduced, IdeS digested NIST reference material 8671 as observed using a 2.1×50 mm BioResolve RP mAb Polyphenyl 450 Å 2.7 µm column with 0.1% TFA mobile phase modifier, according to an illustrative embodiment of the technology.
Figure 1C:
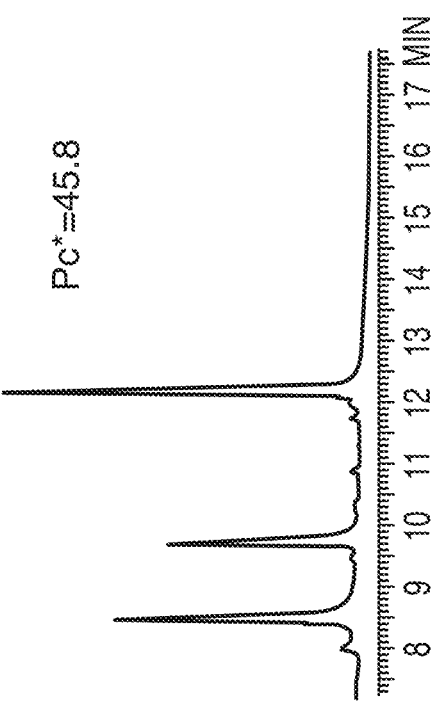
FIG. 1C is a chromatogram for reduced, IdeS digested NIST reference material 8671 as observed using a 2.1×50 mm AMT Halo Protein C4 400 Å 3.4 µm column with 0.1% TFA mobile phase modifier, according to an illustrative embodiment of the technology.
Figure 1B:
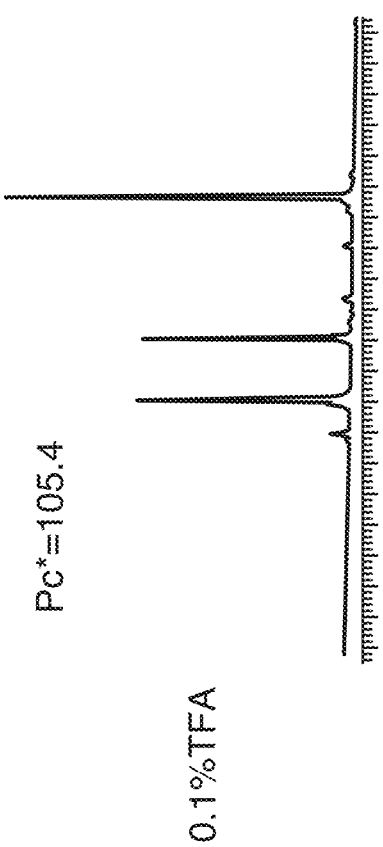
FIG. 1B is a chromatogram for reduced, IdeS digested NIST reference material 8671 as observed using a 2.1×50 mm BioResolve RP mAb Polyphenyl 450 Å 2.2 µm column with 0.1% FA (formic acid) mobile phase modifier, according to an illustrative embodiment of the technology.
Figure 1D:
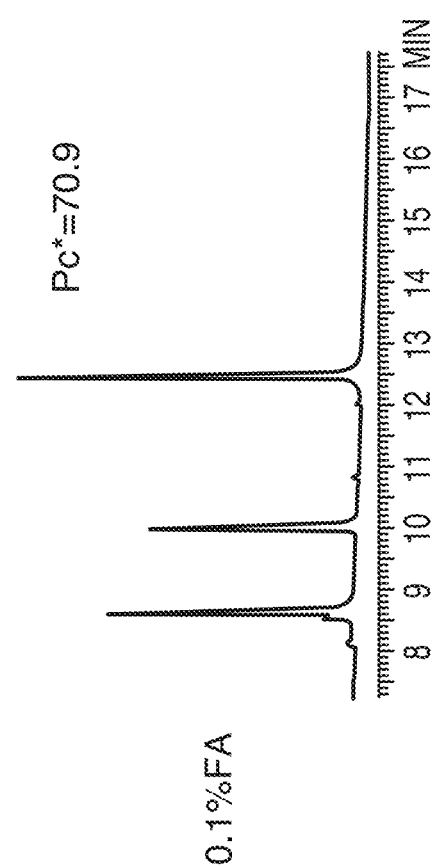
FIG. 1D is a chromatogram for reduced, IdeS digested NIST reference material 8671 as observed using a 2.1×50 mm AMT Halo Protein C4 400 Å 3.4 µm column with 0.1% FA mobile phase modifier, according to an illustrative embodiment of the technology.
Figure 1I:
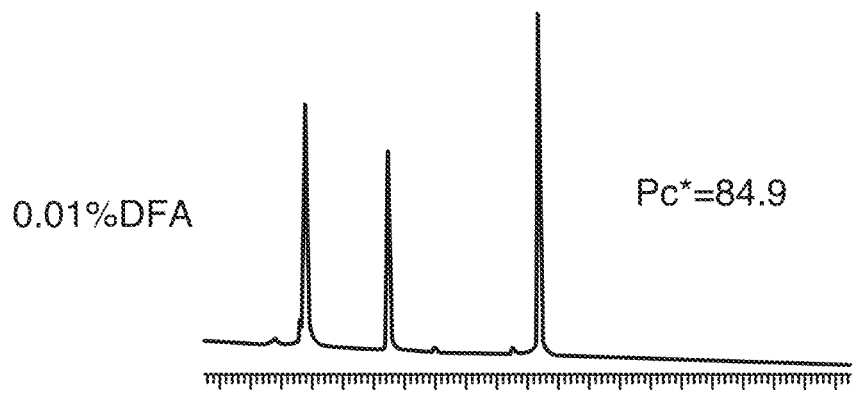
FIG. 1I is a chromatogram for reduced, IdeS digested NIST reference material 8671 as observed using a 2.1×50 mm BioResolve RP mAb Polyphenyl 450 Å 2.7 µm column with 0.01% DFA mobile phase modifier, according to an illustrative embodiment of the technology.
Figure 1J:
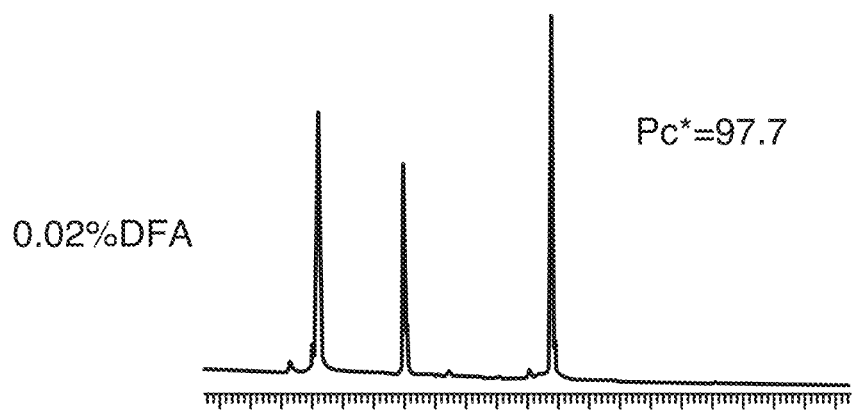
FIG. 1J is a chromatogram for reduced, IdeS digested NIST reference material 8671 as observed using a 2.1×50 mm BioResolve RP mAb Polyphenyl 450 Å 2.7 µm column with 0.02% DFA mobile phase modifier, according to an illustrative embodiment of the technology.
Figure 1K:
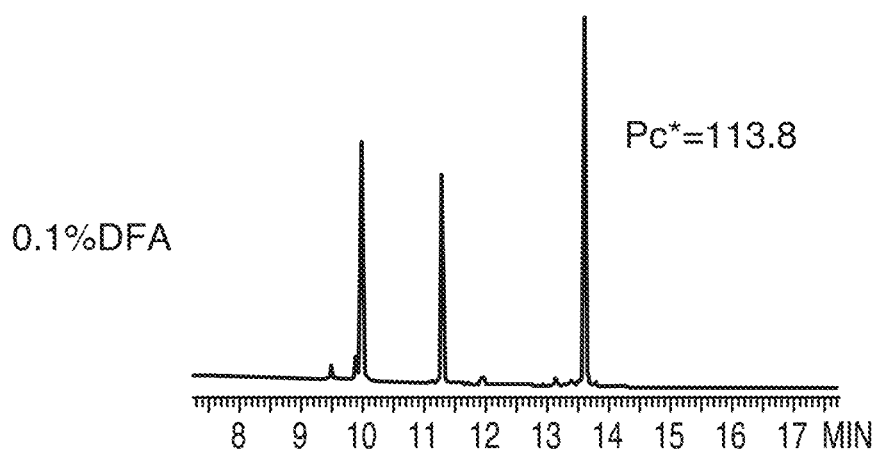
FIG. 1K is a chromatogram for reduced, IdeS digested NIST reference material 8671 as observed using a 2.1×50 mm BioResolve RP mAb Polyphenyl 450 Å 2.7 µm column with 0.1% DFA mobile phase modifier, according to an illustrative embodiment of the technology.
Figure 1L:
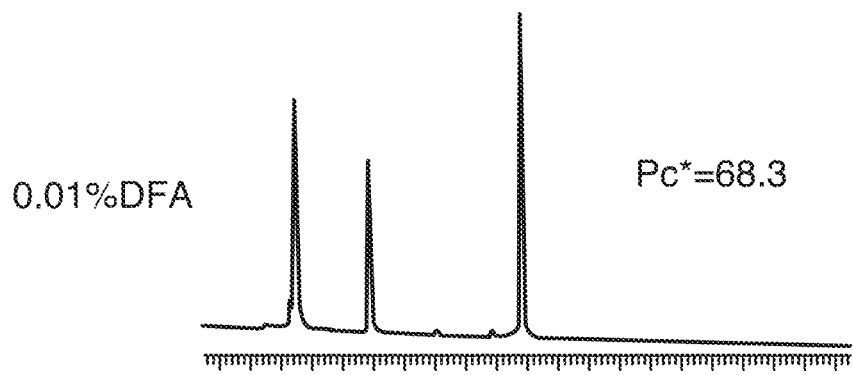
FIG. 1L is a chromatogram for reduced, IdeS digested NIST reference material 8671 as observed using a 2.1×50 mm AMT Halo Protein C4 400 Å 3.4 µm column with 0.01% DFA mobile phase modifier, according to an illustrative embodiment of the technology.
Figure 1M:
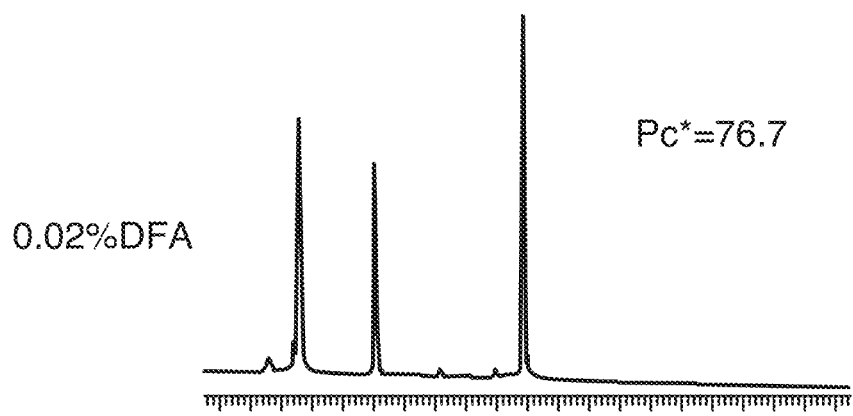
FIG. 1M is a chromatogram for reduced, IdeS digested NIST reference material 8671 as observed using a 2.1×50 mm AMT Halo Protein C4 400 Å 3.4 µm column with 0.02% DFA mobile phase modifier, according to an illustrative embodiment of the technology.
Figure 1N:
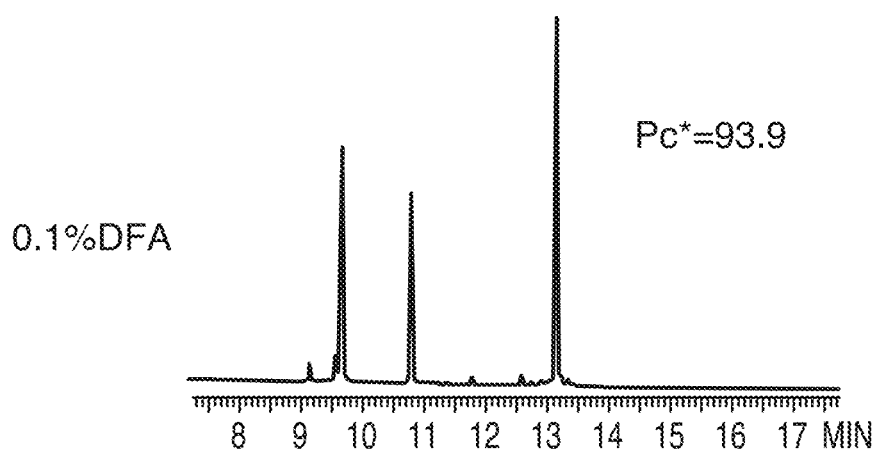
FIG. 1N is a chromatogram for reduced, IdeS digested NIST reference material 8671 as observed using a 2.1×50 mm AMT Halo Protein C4 400 Å 3.4 µm column with 0.1% DFA mobile phase modifier, according to an illustrative embodiment of the technology.
Figure 1O:
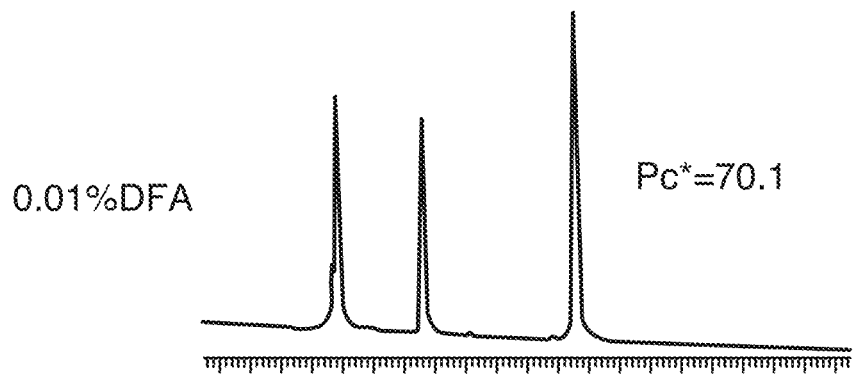
FIG. 1O is a chromatogram for reduced, IdeS digested NIST reference material 8671 as observed using a 2.1×50 mm Agilent AdvanceBio RP-mAb Diphenyl 450 Å 3.5 µm column with 0.01% DFA mobile phase modifier, according to an illustrative embodiment of the technology.
Figure 1P:
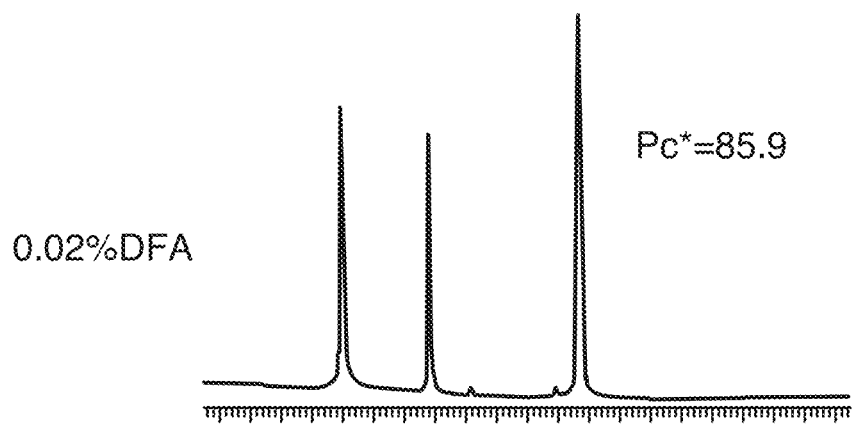
FIG. 1P is a chromatogram for reduced, IdeS digested NIST reference material 8671 as observed using a 2.1×50 mm Agilent AdvanceBio RP-mAb Diphenyl 450 Å 3.5 µm column with 0.02% DFA mobile phase modifier, according to an illustrative embodiment of the technology.
Figure 1Q:
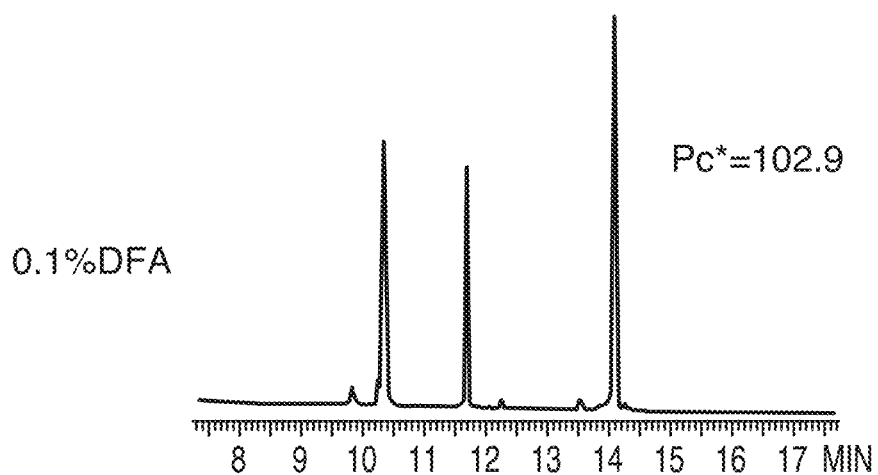
FIG. 1Q is a chromatogram for reduced, IdeS digested NIST reference material 8671 as observed using a 2.1×50 mm Agilent AdvanceBio RP-mAb Diphenyl 450 Å 3.5 µm column with 0.1% DFA mobile phase modifier, according to an illustrative embodiment of the technology.
Figure 1R:
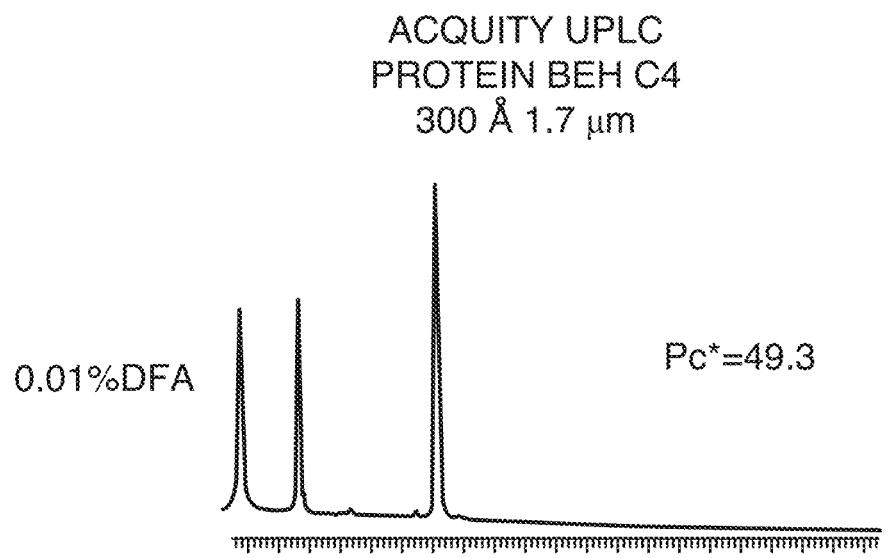
FIG. 1R is a chromatogram for reduced, IdeS digested NIST reference material 8671 as observed using a 2.1×50 mm Acquity UPLC Protein BEH C4 300 Å 1.7 µm column with 0.01% DFA mobile phase modifier, according to an illustrative embodiment of the technology.
Figure 1S:
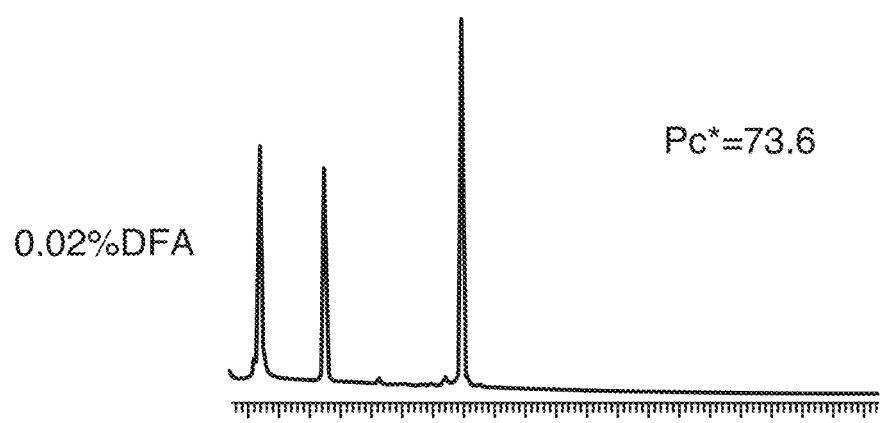
FIG. 1S is a chromatogram for reduced, IdeS digested NIST reference material 8671 as observed using a 2.1×50 mm Acquity UPLC Protein BEH C4 300 Å 1.7 µm column with 0.02% DFA mobile phase modifier, according to an illustrative embodiment of the technology.

The present disclosure relates to methods based on low concentrations of an alternative acid, difluoroacetic acid ("DFA"), used with or without phenyl-based stationary phases that are capable of yielding unforeseen optimization of both chromatographic and mass spectrometric performance. The technology also includes a composition of DFA having low level metal impurities, for example, less than about 100 ppb of any individual metal impurity. The purity of DFA leads to the ability to achieve mass spectrometry (MS) quality sufficient for a DFA based liquid chromatography-mass spectrometry ("LC-MS") method to produce interpretable data.

While the present disclosure discusses the technology in relation to difluoroacetic acid, dichloroacetic acid or dibromoacetic acid can also be used and are expected to show similar results with respect to unforeseen optimization of both chromatographic and mass spectrometric performance. In addition, while the present disclosure discusses the technology mainly in relation to proteins, the methods can also be applied to other biomolecules, including, for example, peptides and glycans. Moreover, the reagent and methods of the present technology are also applicable to the analysis of peptides and the peptide mapping of protein therapeutics.

In addition, while the present disclosure first discusses the technology in relation to biomolecules, the methods and kits can be applied to other analytes, such as small molecules. In connection with the technology related to small molecules, the purity of the DFA to limit the level of any impurity (i.e., not just metals) to less than about 100 ppb of any individual impurity is desired. To reduce or eliminate contaminates during the purification process (e.g., during distillation of the DFA) fluoropolymer vessels (e.g., PFA vessels for storing, condensing, and collecting the DFA) may be utilized.

As used herein, the term "resolution" refers to the measure of how well two peaks are separated. Resolution can be determined by $R_s=(t_{r,2}-t_{r,1})/(0.5\times(w_1+w_2))$, wherein $t_r$ is the retention time of either peak 1 or peak 2, and $w_1$ is the peak width at half height for peak 1 or peak 2. In a similar fashion, resolving power and peak capacity are used to refer to the measure of how many peaks can fit within a given separation space. Peak capacity can be determined as $P_c=1+(t/w_{avg})$, wherein t is the time corresponding to the given separation space and $w_{avg}$ is the average peak width at half height observed for peaks in a given separation.

The term "protein" as used herein, refers to a polymeric chain of amino acids called polypeptides. A protein may also include a number of modifications, including phosphorylation, lipidation, prenylation, sulfation, hydroxylation, acetylation, addition of carbohydrate (glycosylation and glycation), addition of prosthetic groups or cofactors, formation of disulfide bonds, proteolysis, assembly into macromolecular complexes and the like.

The term "small molecule" as used herein, refers to a low molecular weight (i.e., under 900 daltons), organic compound that can be either biological or synthetic in origin. Some examples of small molecules include, but are not limited to 2,6-Dimethylaniline, Toluidine, 4-Chloro-N-methylaniline, Histidine, 2-Chloro-E-nitroaniline, Thiamine, Tryptophan, Guanosine-5'-monophosphate (G5MP), Thymidine-5'-monophaste (T5MP), and Niflumic Acid.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

In concept, DFA is a more MS-friendly alternative to TFA for protein LC-MS. DFA is 10 times less acidic than TFA, so it can be less detrimental to MS detection. Being a weaker acid, it is likely to form weaker ion pair interactions with analyte cations. In turn, DFA may show a lower propensity than TFA to produce adducts in mass spectra. Moreover, being composed of only two fluorine atoms, versus the three of TFA, DFA is less likely to adsorb to materials and to be problematically retained throughout LC flow paths and MS ion paths, which has been an annoyance for some LC-MS scientists in their attempts to use TFA.

However, the appeal of DFA cannot be fully appreciated by speculation alone. As shown in the scope of this technology, there is more to the quality of protein LC-MS than just ionization efficiency. With this technology, a composition of DFA is specified that ensures the production of high quality protein mass spectra. This composition of DFA can be provided in kits, along with a chromatography column and instructions for use. In addition, novel methods are defined for protein LC-MS that call for DFA to be used at unconventionally low concentrations, with or without a phenyl based stationary phase. Further, this technology provides a method of purifying commercially available difluoroacetic acid to obtain a high-purity difluoroacetic acid containing less than 100 ppb of a metal impurity. In some embodiments, the method of purifying can include use of fluoropolymer distilling equipment (e.g., reservoirs, condensers, vessels, etc,) to reduce or eliminate contaminates such that the high-purity difluoroacetic acid contains less than 100 ppb of any individual impurity. As a result, the methods can be extended to small-molecule LC-MS analysis.

Biomolecule (e.g., protein, peptide, and/or glycan) LC-MS is not merely about achieving high sensitivity detection. The capability of the method is greatly impacted by the resolution of the chromatography. Interestingly, DFA mobile phases can actually provide gains in resolution as compared to TFA. This was a surprising result given that formic acid, a weaker, less hydrophobic acid, leads to astoundingly lower peak capacity versus TFA. Accordingly, it was assumed that a more acidic, more hydrophobic mobile phase additive would always yield better chromatographic resolving power. While not limited to theory, it is believed that DFA is more effective than TFA in producing high resolution chromatography because it exhibits less steric bulk. Consequently, it is likely for DFA to more effectively and more extensively interact with protein analytes and the bonded phase of an RPLC stationary phase. It might also be that the hydrophobicity of DFA, being attenuated from that of TFA, facilitates more optimal protein adsorption, partitioning, and desorption.

Figure 1T:
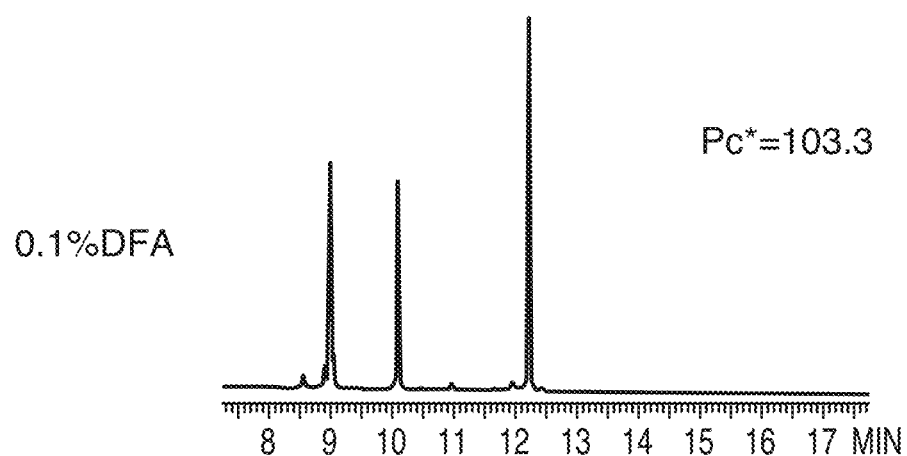
FIG. 1T is a chromatogram for reduced, IdeS digested NIST reference material 8671 as observed using a 2.1×50 mm Acquity UPLC Protein BEH C4 300 Å 1.7 µm column with 0.1% DFA mobile phase modifier, according to an illustrative embodiment of the technology.
Figures 2A, 2B:
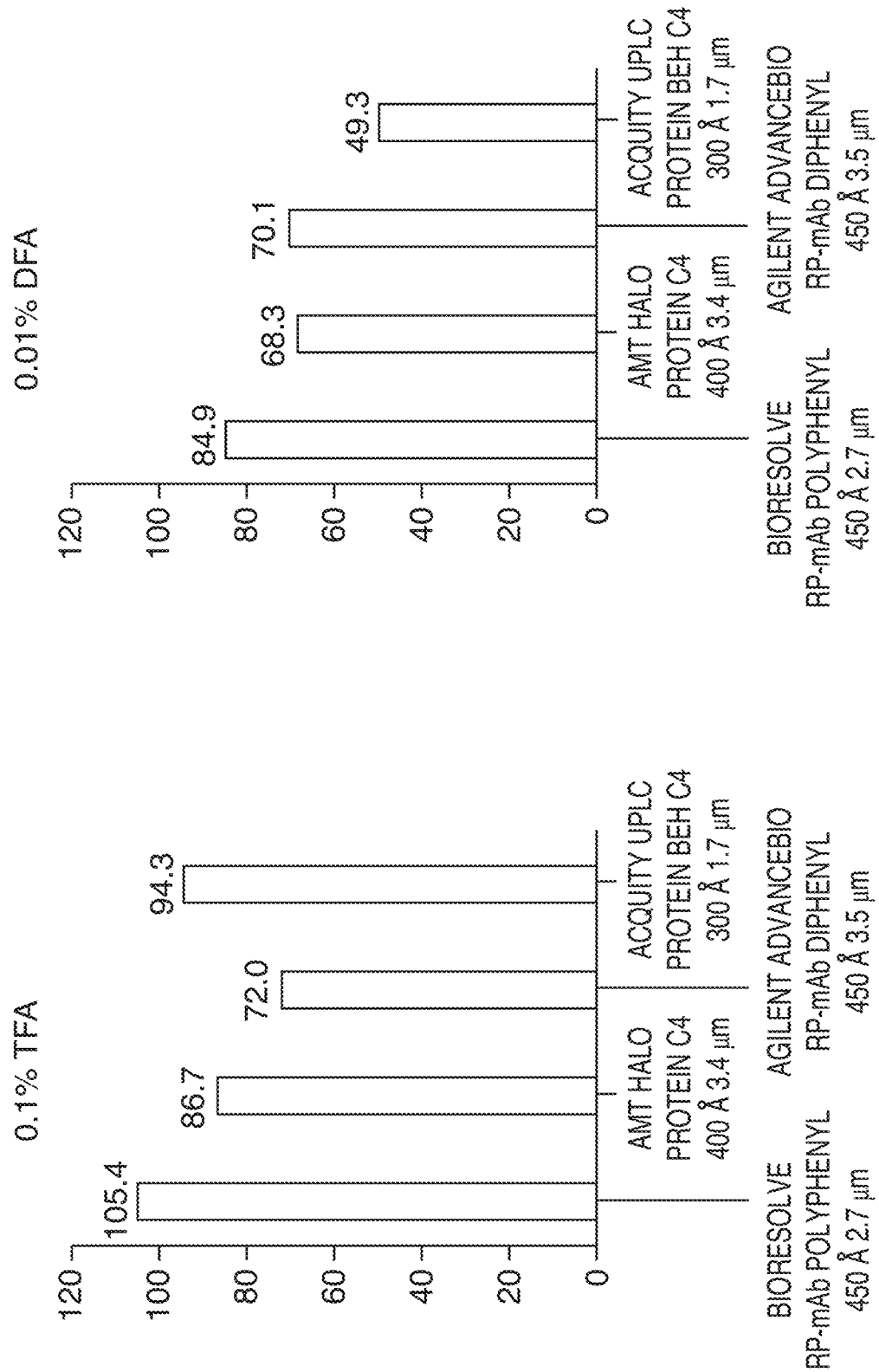
FIG. 2A is a graph showing effective peak capacity values for reduced, IdeS digested NIST reference material 8671 as observed using various 2.1×50 mm columns and 0.1% TFA mobile phase modifier, according to an illustrative embodiment of the technology.
FIG. 2B is a graph showing effective peak capacity values for reduced, IdeS digested NIST reference material 8671 as observed using various 2.1×50 mm columns and 0.01% DFA mobile phase modifier. according to an illustrative embodiment of the technology.
Figures 2C, 2D:
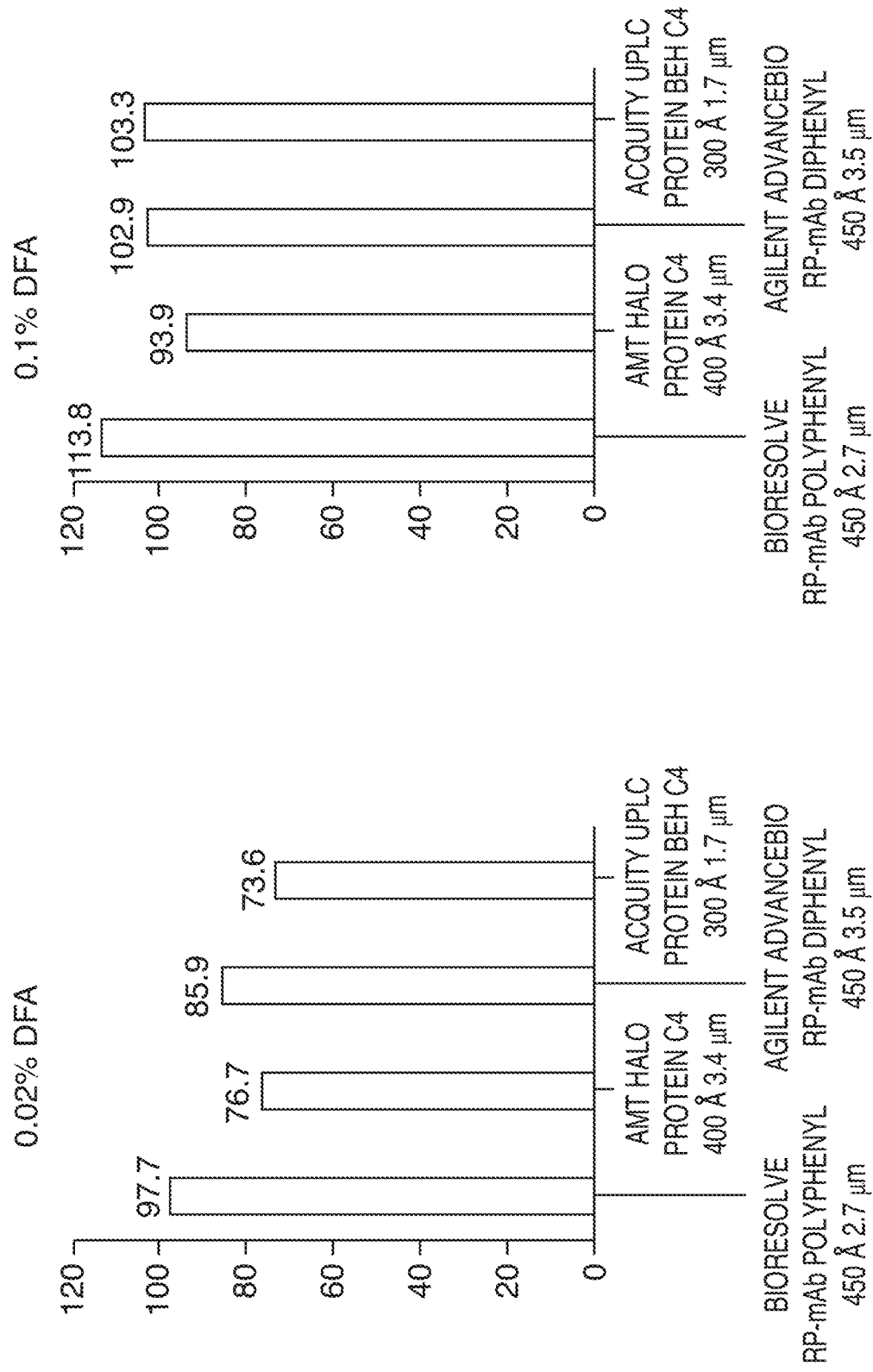
FIG. 2C is a graph showing effective peak capacity values for reduced, IdeS digested NIST reference material 8671 as observed using various 2.1×50 mm columns and 0.02% DFA mobile phase modifier, according to an illustrative embodiment of the technology.
FIG. 2D is a graph showing effective peak capacity values for reduced, IdeS digested NIST reference material 8671 as observed using various 2.1×50 mm columns and 0.1% DFA mobile phase modifier, according to an illustrative embodiment of the technology.
Figure 2E:
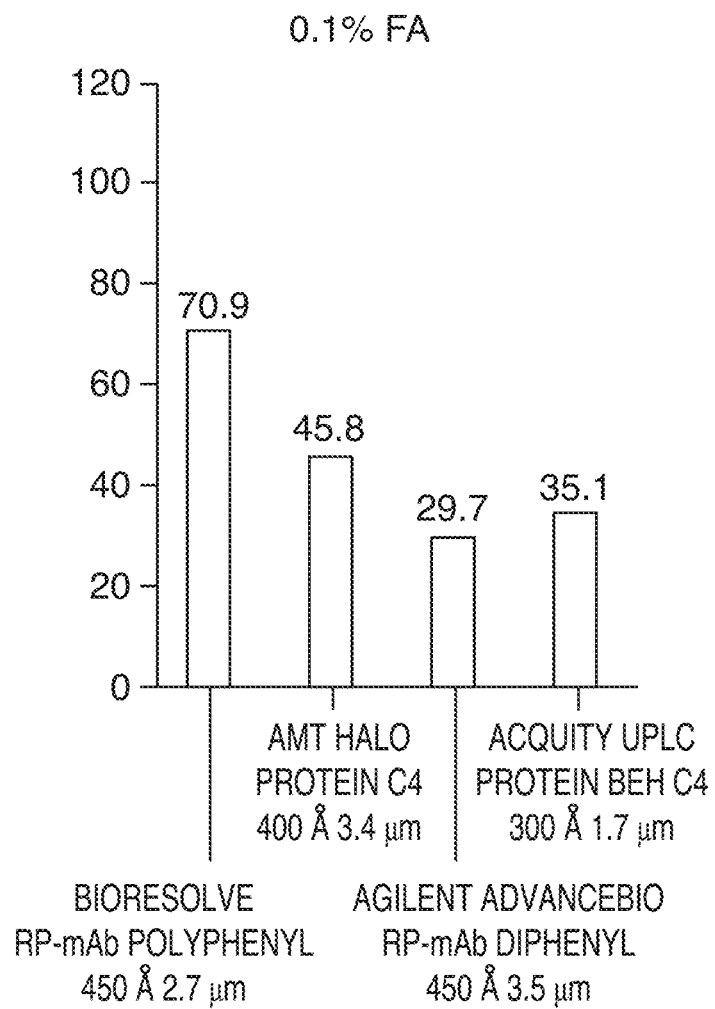
FIG. 2E is a graph showing effective peak capacity values for reduced, IdeS digested NIST reference material 8671 as observed using various 2.1×50 mm columns and 0.1% FA mobile phase modifier, according to an illustrative embodiment of the technology.

FIGS. 1A-1T show the effective peak capacity values for reduced IdeS digested NIST reference material 8671 as observed using various 2.1×50 mm columns, including (1) Waters BioResolve™ RP mAb Polyphenyl, 450 Å 2.7 µm; (2) AMT HALO® Protein C4, 400 Å 3.4 µm; (3) Agilent AdvanceBio® RP-mAb Diphenyl 450 Å 3.5 µm; and (4) Waters ACQUITY® UPLC®, Protein BEH C4, 300 Å 1.7 µm. FIGS. 2A-E show effective peak capacity values for reduced, IdeS digested NIST reference material 8671 as observed using each of the various columns of FIGS. 1A-1T. The specifics of the analysis can be found in Example 1, herein.

As shown in an evaluation of these various column technologies, 0.1% (v/v) DFA can yield significantly higher peak capacities versus 0.1% (v/v) TFA. In particular, for separations of reduced, IdeS digested NIST reference material 8671, it has been seen that there can be increases corresponding to up to about 40% gains in effective peak capacity. For example, the effective peak capacity using IdeS digested NIST reference material 8671 with Agilent AdvanceBio® RP-mAb Diphenyl 450 Å 3.5 µm is 72.0 when using 0.1% (v/v) TFA as a mobile phase, but increases to 102.9 when using 0.1% (v/v) DFA, resulting in more than a 40% gain in effective peak capacity. In addition, the Agilent column showed about a 20% gain in effective peak capacity when using 0.02% (v/v) DFA as compared with a higher concentration, 0.1% (v/v) TFA. Moreover, there was only a slight decrease, less than 5%, in effective peak capacity when 0.01% (v/v) DFA was used with the Agilent column as compared to 0.1% (v/v) TFA.

As shown in FIGS. 1A-1T, and 2A-E, all chromatography columns showed an increase in effective peak capacity when using 0.1% DFA compared to 0.1% TFA. The other three columns each showed about a 10% gain in effective peak capacity when using 0.1% (v/v) DFA compared to 0.1% (v/v) TFA.

These gains can also be seen when profiling samples produced by other enzymes including IdeZ, Lys-C, and papain as well as enzymes commercially available from Genovis AB (Lund, Sweden) under the tradename FabULOUS®, FabRICATOR®, FabALACTICA® and GingisKHAN®. Even more notably, a superficially porous silica stationary phase bonded with phenyl moieties in a multistep silanization process has been found to provide exemplary performance capabilities with a DFA mobile phase. With this stationary phase, performance is surprisingly good even with low concentrations of DFA additive. FIGS. 1A-1T, and 2A-E show that, indeed, when 0.01 and 0.02% DFA mobile phases are used along with this sort of stationary phase material, exemplary resolving power is produced. However, it is not just the gain in effective peak capacity that results when a superficially porous stationary phase bonded with phenyl moieties in a multistep salinization process that provides exemplary performance, but also the percentage of phenyl coverage on the surface of the stationary phase. For example, the column commercially available from Waters Corporation (Milford, Mass.) under the tradename BioResolve™ RP mAb Polyphenyl, has about 10% phenyl coverage making it less dependent on ion pairing. Stationary phases that can be advantageously used with these unique conditions have been described in United States publication no. 2018/0264438 entitled "Chromatographic Compositions" assigned to Waters Technologies Corporation, which is incorporated herein by reference in its entirety.

Figure 3B:
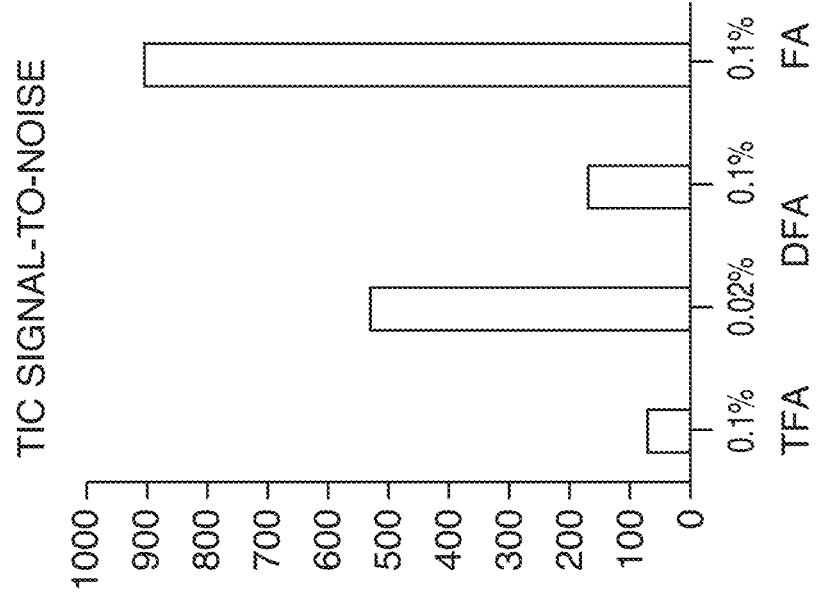
FIG. 3B is a graph showing LC-MS sensitivity for the detection of the light chain subunit of reduced, IdeS digested NIST reference material 8671 as observed using an LC column commercially available from Waters Corporation (Milford, Mass.) under the tradename BioResolve™ RP mAb Polyphenyl 2.1×50 mm column and a detector commercially available from Waters Corporation (Milford, Mass.) under the tradename ACQUITY® QDa® single quadrupole mass detector.
Figure 3A:
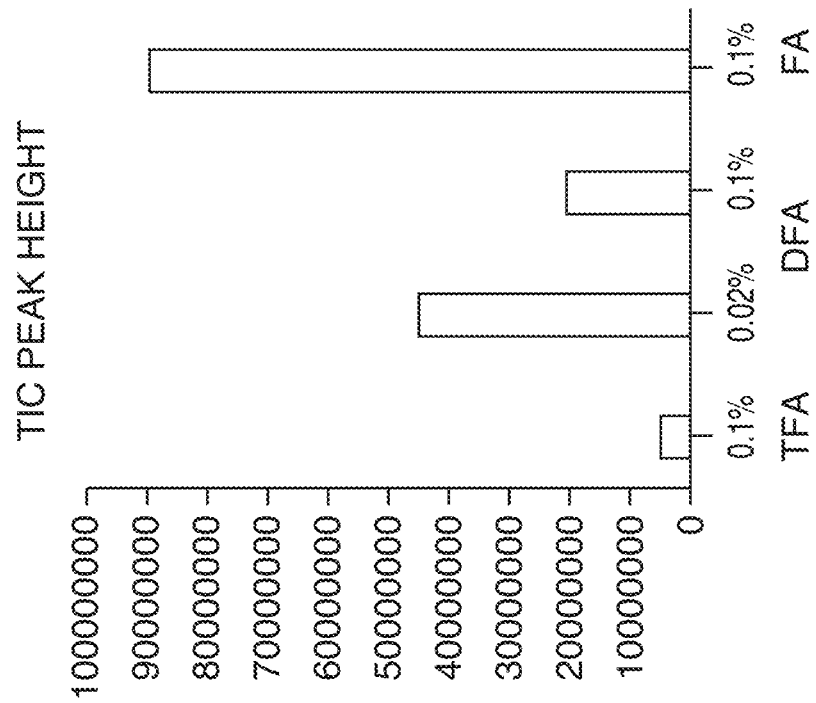
FIG. 3A is a graph showing LC-MS sensitivity for the detection of the light chain subunit of reduced, IdeS digested NIST reference material 8671 as observed using an LC column commercially available from Waters Corporation (Milford, Mass.) under the tradename BioResolve™ RP mAb Polyphenyl 2.1×50 mm column and a detector commercially available from Waters Corporation (Milford, Mass.) under the tradename ACQUITY® QDa® single quadrupole mass detector.

It is noteworthy to have discovered that an exemplary level of chromatographic performance is possible even with the use of just 0.01% and 0.02% (v/v) DFA, because it has proven to be of benefit to the sensitivity of MS detection. FIGS. 3A and 3B show LC-MS sensitivity for the detection of the light chain subunit of reduced, IdeS digested NIST reference material 8671 as observed using an LC column commercially available from Waters Corporation (Milford, Mass.) under the tradename BioResolve™ RP mAb Polyphenyl 2.1×50 mm column and an MS detector commercially available from Waters Corporation (Milford, Mass.) under the tradename ACQUITY® QDa® single quadrupole mass detector. FIG. 3A shows total ion chromatogram ("TIC") peak heights resulting from the use of various mobile phase modifiers. FIG. 3B shows TIC signal-to-noise resulting from the use of various mobile phase modifiers. The specifics of the analysis can be found in Example 2, herein.

TIC peak height and TIC peak signal-to-noise ratio are two values that are frequently used to define the sensitivity of an LC-MS analysis. When various mobile phase systems were employed to detect reduced, IdeS digested NIST reference material 8671 with an MS detector commercially available from Waters Corporation (Milford, Mass.) under the tradename ACQUITY® QDa® single quadrupole mass detector, substantially different values for MS sensitivity were observed. When 0.1% (v/v) DFA was used in place of 0.1% (v/v) TFA, an approximately 4 fold increase in MS sensitivity was achieved. Furthermore, when 0.02% (v/v) DFA was used in place of 0.1% (v/v) TFA, an approximately 8 fold increase in MS sensitivity was achieved. That a protein RPLC method is able to produce near optimal resolution under such conditions means that a new standard for high resolution, high sensitivity LC-MS of proteins has been established.

Accordingly, a method is provided for separating an analyte from a sample. The analyte can be a biomolecule, for example, a protein, peptide, glycan, or combination thereof. The method includes flowing a mobile phase through a chromatography column. The mobile phase can be a halogenated acid, for example, DFA, dichloroacetic acid or dibromoacetic acid. The mobile phase can include about 0.005% (v/v) to about 0.20% (v/v) halogenated acid. In addition, the mobile phase can have less than about 100 ppb of any individual metal impurity. In other words, all metal impurities in the mobile phase halogenated acid are each less than 100 ppb, but combined, can be greater than 100 ppb. A sample that comprises the analyte is injected into the mobile phase and then the analyte is separated from the sample.

The analyte can be separated from the sample through chromatography. A person having ordinary skill in the art would understand that many different types of chromatography can be used with the method. For example, the method can be applied to liquid chromatography, RPLC, UHPLC, HPLC, and hydrophilic interaction chromatography ("HILIC"). Therefore, a liquid chromatography column, reverse phase chromatography column, ultra-performance chromatography column, high-performance chromatography, and hydrophilic interaction chromatography columns can be used in the method.

In an embodiment of this technology, a high sensitivity, high resolution protein RPLC method is achieved using a DFA modified mobile phase in combination with column stationary phase having a phenyl-based surface chemistry. The chromatography column can include a stationary phase having phenyl-based surface chemistry. The stationary phase can be either a fully porous or a superficially porous silica stationary phase bonded with phenyl moieties. The stationary phases can include, but are not limited to, those found in reverse phase columns commercially available from Agilent Technologies (Santa Clara, Calif.) under the tradenames AdvanceBio® RP mAb Diphenyland Zorbax® RRHD Diphenyl, and Waters Corporation (Milford, Mass.) under the tradename BioResolve™ RP mAb Polyphenyl columns as well as the materials described in United States publication no. 2018/0264438 entitled "Chromatographic Compositions" assigned to Waters Technologies Corporation, which is incorporated herein by reference in its entirety.

In some embodiments, the stationary phase can have a polymeric polystyrene divinyl benzene surface chemistry. In another embodiment, the stationary phase can be based on organosilica bonded with phenyl moieties. These stationary phases can be found, for example, in columns commercially available Agilent Technologies (Santa Clara, Calif.) under the tradename PLRP-S® and from Waters Corporation (Milford, Mass.) under the tradename ACQUITY® UPLC® BEH Phenyl, respectively.

Chromatography columns of the present technology can be used along with concentrations of about 0.005 to about 2.5%% (v/v) DFA mobile phase. Any concentration of mobile phase within this range can be used with the disclosed methods, kits, and compositions. For example, a 0.01 to 0.05% (v/v) DFA mobile phase can be used with a chromatography column, e.g., an RPLC column. In another example, a 0.02% (v/v) to 0.05% (v/v) DFA mobile phase can be used with a chromatography column, e.g., an RPLC column. In another embodiment, a 0.01% (v/v) to 0.2% (v/v) DFA mobile phase is used. Some embodiments feature higher concentrations, such as for example a concentration range of about 0.1 to about 0.9% (v/v) DFA mobile phase or a concentration range of 0.5 to 2.0% (v/v) DFA mobile phase.

In addition to chromatographic resolution, protein LC-MS methods are also judged by the quality of the mass spectra they provide. No work has yet been performed regarding the quality of mass spectra produced by DFA mobile phases, as evidenced by the fact that commercially available sources of DFA produce low quality mass spectra. FIG. 4 shows deconvoluted ESI mass spectra for the light chain subunit of NIST reference material 8671 as observed using (a) 0.1% (v/v) TFA and (b) 0.1% (v/v) DFA with a mass spectrometer commercially available from Waters Corporation (Milford, Mass.) under the tradename Synapt® G2-Si. The relative intensities of undesirable ion adducts, including Na and K are reported. The specifics of the analysis can be found in Example 3, herein.

As shown in FIGS. 4A and 4B, a mass spectrum obtained for a light chain monoclonal antibody (mAb) subunit using 0.1% (v/v) DFA (Oakwood, part number 001231, lot D06N) produced very high ion intensities for sodiated (+Na) and potassiated (+K) ions. This was a level of ion intensity (approximately 6-7%) that impaired the interpretation of the mass spectrum. In contrast, a mass spectrum collected from LC-MS with a 0.1% (v/v) TFA mobile phase showed a mass spectrum of significantly greater quality, being that the sodiated and potassiated ions accounted for relative intensities of less than or equal to 2%. While not limited to theory, it might be possible that a particular acid has not only an effect on formation of the analyte ions but also a differential effect on the formation of adducts. Regardless, it is reasoned that the commercially available DFA reagents are not fit for LC-MS, because it has not yet been realized that in order to achieve desirable mass spectral quality substantially higher purity DFA must be manufactured, most specifically low metal content DFA. That is, there is a correlation between certain impurities and the desirable features of a protein mass spectrum.

FIG. 5 shows metal impurities quantified by inductively coupled plasma (ICP)-MS in a sample of DFA (Oakwood, part number 001231, lot D06N). Concentrations are reported in part per billion ("ppb"). A sample of DFA (Oakwood, part number 001231, lot D06N) was subjected to ICP-MS to quantify its metal impurities (FIG. 5), whereby it was found that the DFA did in fact contain relatively high levels of metals, including sodium at a concentration of 1500 ppb. Without question, this level of metal content is too high for it to be possible to obtain a high quality protein mass spectrum.

DFA-derived, deconvoluted spectra showed significant interference from potassium and sodium adducts, as demonstrated in FIG. 6A. In corroboration of this result, ICP-MS quantitation of the employed DFA showed it to contain 400 ppm sodium and 2 ppm potassium (FIG. 6B). Interestingly, two other commercial sources of DFA were also confirmed to have these same problematically high concentrations (data not shown). To address this shortcoming, commercially-sourced DFA was distilled to higher purity using an apparatus constructed from chemically-resistant perfluoroalkoxy alkane (PFA) polymer. ICP-MS results indicated that, by means of this distillation, sodium and potassium content of the DFA could be reduced to a concentration of less than 20 ppb. When used for LC-MS, this distilled DFA afforded spectra with adduct levels lowered to relative intensities of only 2% (FIG. 6C).

The methods of the present technology include the use of a mobile phase additive that includes less than about 100 ppb of any individual metal impurity. In other words, each metal impurity contained in the mobile phase additive is not present in an amount greater than about 100 ppb. In some embodiments, the mobile phase comprises less than about 90 ppb, 80 ppb, 70, ppb, 60, ppb, 50 ppb, 40 ppb, 30 ppb, 20 ppb, or 10 ppb of any individual metal impurity. In some embodiments, the mobile phase additive comprises less than about 95 ppb, 85 ppb, 75, ppb, 65, ppb, 55 ppb, 45 ppb, 35 ppb, 25 ppb, or 15 ppb of any individual metal impurity. The metal impurity is any metal that affects the desirable features of a mass spectrum, e.g., the quality of the mass spectrum. The metal impurity can be, for example, sodium, potassium, calcium and/or iron. These aspects of the technology extend to any dilutions and to any mobile phases that are subsequently prepared with the above described mobile phase additive.

The methods can include detecting the analyte with a mass spectrometer. This can be accomplished by generating analyte ions. The analyte ions can be generated by electrospray ionization or desorption electrospray ionization.

The mass spectrometer can produce a mass spectrum having less than about 5% relative ion intensity corresponding to metal or salt adducts. The mass spectrometer can produce a mass spectrum having less than about 5% relative ion intensity corresponding to metal or salt adducts when the mobile phase additive includes less than about 100 ppb of any individual metal impurity. In some embodiments, the mass spectrometer can produce a mass spectrum having less than about 2%, or less than about 1%, relative ion intensity corresponding to metal or salt adducts.

The methods described herein can also include determining the molecular weight of the analyte, for example, determining the molecular weight of the protein, peptide, glycan, or combination thereof. Likewise, the methods described herein can be used to facilitate determining the location of certain post-translational modifications, as can be performed by RPLC-MS/MS experiments.

The technology also includes methods of purifying commercially available halogenated acids. For example, a commercially available halogenated acid (e.g., DFA, dichloroacetic acid or dibromoacetic acid) can be obtained. The halogenated acid contains greater than 100 ppb of a metal impurity. The metal impurity is sodium, potassium, calcium, iron or combinations thereof. The method includes distilling the halogenated acid to obtain a high-purity difluoroacetic acid containing less than 100 ppb of the impurity. In some embodiments, the halogenated acid contains less than 50 ppb or less than 20 ppb of the impurity.

The commercially available halogenated acid can be purified by other methods, for example, by filtering, centrifuging, evaporation, extraction, ion exchange, or any combination.

The technology comprises a composition of a volume of difluoroacetic acid, ranging from 10 µL to 10 mL, containing less than 100 ppb of individual metal impurities, including but not limited to sodium, potassium, calcium and/or iron, that is purposed for LC-MS analyses of proteins, wherein the use of such a reagent facilitates the production of protein mass spectra having less than 5% relative ion intensity corresponding to metal and/or salt adducts, including but not limited to sodium, potassium, calcium and/or iron. The use of the high purity composition of this technology can facilitate the production of protein mass spectra having less than 2% (and possibly even less than 1%) relative ion intensity corresponding to metal and/or salt adducts, including but not limited to sodium, potassium, calcium and/or iron. In some embodiments, the use of the high purity composition of this technology can facilitate the production of protein mass spectra having less than 1% relative ion intensity corresponding to metal and/or salt adducts, including but not limited to sodium, potassium, calcium and/or iron The compositions of the halogenated acid can be made commercially available in the form of ready-to-use ampoules as well as a component of a kit, such as a combined product comprised of an ampoule containing the composition of this technology along with an LC column or device. For example, the kit can include a chromatography column, an ampoule having a volume of mobile phase additive, and instructions for use. The chromatography column has a stationary phase material inside the column. The stationary phase material can be any stationary phase material described herein, for example, a superficially porous silica stationary phase bonded with phenyl moieties, a fully porous silica stationary phase bonded with phenyl moieties, an organosilica stationary phase bonded with phenyl moieties, or a polymeric polystyrene divinyl benzene surface chemistry. The mobile phase additive is a halogenated acid, for example, DFA. The mobile phase additive has less than about 100 ppb of any individual metal impurity. The instructions instruct the user to obtain a sample containing at least one biomolecule (e.g., a protein) in a sample matrix as well as to dilute the mobile phase additive with a solvent to obtain about 0.005% (v/v) to about 0.20% (v/v) halogenated acid (e.g., DFA). Like the DFA mobile phase additive, the solvents are to have less than about 100 ppb of any individual metal impurity, or less than about 95 ppb, 85 ppb, 75, ppb, 65, ppb, 55 ppb, 45 ppb, 35 ppb, 25 ppb, or 15 ppb of any individual metal impurity. The user is then instructed to flow the sample with the diluted mobile phase through the column to substantially resolve and retain the at least one biomolecule (e.g., protein). In addition, the instructions instruct the user to detect the at least one biomolecule (e.g., protein) using a detector.

In addition to kits for analysis of biomolecules, the present technology includes kits for the analysis of small molecules. In these embodiments, the DFA is distilled utilizing fluoropolymer vessels (e.g., reservoirs, condensers) to reduce leaching in of contaminates into the highly-purified DFA before, during, and/or after the purification process. As a result, the highly-purified DFA includes less than about 100 ppb of any individual impurity.

Similarly, the composition of the halogenated acid extends to ready-to-use mobile phases. A container of the ready-to-use mobile phase can be included as part of a kit. The kit also includes a chromatography column and instructions for use. The chromatography column has a stationary phase material inside the column. The stationary phase material can be any stationary phase material described herein, for example, a fully or superficially porous silica stationary phase bonded with phenyl moieties, an organosilica stationary phase bonded with phenyl moieties, or a polymeric polystyrene divinyl benzene surface chemistry. The mobile phase is about 0.005% (v/v) to about 2.50% (v/v) halogenated acid (e.g., DFA) and less than about 100 ppb of any individual impurity, including metal impurities. The instructions instruct the user to obtain a sample of at least one biomolecule (e.g., a protein) or at least one small molecule in a sample matrix. The user is then instructed to flow the sample with the mobile phase through the column to substantially resolve and retain the at least one biomolecule (e.g., protein) or at least one small molecule. In addition, the instructions instruct the user to detect the at least one biomolecule (e.g., protein) or at least one small molecule using a detector.

In common practice, an LC mobile phase is prepared by adding a small (10 µL to 10 mL) volume of liquid additive, conventionally formic acid or trifluoroacetic acid, to a desired solvent, such as water or acetonitrile. To that end, it is intended that this technology cover, but is not limited to, ready-to-use mobile phases based on water, acetonitrile, methanol, propanol, butanol, and pentanol (and combinations thereof) modified with 0.005 to 2.50% (v/v) halogenated acid (e.g., DFA) (that have less than about 100 ppb levels, or less than 50 ppb levels, or less than 20 ppb levels, of individual impurities, especially individual metal impurities, including but not limited to sodium, potassium, calcium and/or iron), that is purposed for LC-MS analyses of proteins, wherein the use of such a reagent facilitates the production of protein mass spectra having less than 5%, less than 2% or less than 1%, relative intensity corresponding to metal and/or salt adducts, including but not limited to sodium, potassium, calcium and/or iron.

EXAMPLES

Example 1: Reversed Phase Chromatography of mAb Subunits

This example compares the effects of three acids, TFA, DFA and formic acid, across four different columns in RPLC systems. Each column separated the same reference material. Runs were performed with 0.1% TFA, 0.1% DFA, 0.02% DFA, 0.01% DFA and 0.1% formic acid based mobile phase modifiers. Summarized below is the basic procedure that was used across all runs. The results are summarized in FIGS. 1A-1T, and 2A-E.

Reduced, IdeS-digested NIST Reference Material 8671, a humanized IgG1κ expressed from a murine cell line, was obtained in the form of the Waters mAb Subunit Standard (Waters, Milford, Mass.). The contents of one vial were reconstituted in 0.1% (v/v) formic acid in water. Analyses of this sample were performed using a LC System sold by Waters Corporation (Milford, Mass.) under the tradename ACQUITY® UPLC® H-Class Bio and a separation method outlined below. FIGS. 1A-1T, and 2A-E present chromatographic data obtained with several different mobile phase systems used in combination with various RPLC columns. The LC conditions are shown in Table 1 and the Gradient Conditions are shown in Table 2.

TABLE 1

| LC Conditions | |
|---|---|
| Columns: | Waters BioResolve ™ RP mAb Polyphenyl, 450 Å 2.7 μm, 2.1 × 50 mm |
| | AMT Halo ® Protein C4, 400 Å 3.4 μm, 2.1 × 50 mm |
| | Agilent AdvanceBio ® RP-mAb Diphenyl, 450 Å 3.5 μm, 2.1 × 50 mm |
| | Waters ACQUITY ® UPLC ®, Protein BEH C4, 300 Å 1.7 μm, 2.1 × 50 mm |
| Mobile Phase A: | 0.01 to 0.1% (v/v) acid in water |
| Mobile Phase B: | 0.01 to 0.1% (v/v) acid in acetonitrile |
| Column Temperature: | 80° C. |
| Injection Volume: | 4 μL |
| Sample Concentration: | 0.25 μg/μL |
| Sample Diluent: | 0.01 to 0.1% (v/v) formic acid in water |
| UV Detection: | 280 nm (10 Hz) |

TABLE 2

| Gradient Table | | | | |
|---|---|---|---|---|
| Time (min) | Flow Rate (mL/min) | % A | % B | Curve |
| Initial | 0.2000 | 85.0 | 15.0 | Initial |
| 20.00 | 0.2000 | 45.0 | 55.0 | 6 |
| 20.30 | 0.2000 | 20.0 | 80.0 | 6 |
| 21.30 | 0.2000 | 20.0 | 80.0 | 6 |

TABLE 2-continued

| Gradient Table | | | | |
|---|---|---|---|---|
| Time (min) | Flow Rate (mL/min) | % A | % B | Curve |
| 21.60 | 0.2000 | 85.0 | 15.0 | 6 |
| 25.00 | 0.2000 | 85.0 | 15.0 | 6 |

Example 2: Mass Spectrometry with a Single Quadrupole Mass Detector

This example was done to compare the effect of using DFA and TFA on MS sensitivity based on TIC peak height and TIC peak signal-to-noise ratio which are used to define the sensitivity of an LC-MS analysis. Various mobile phase systems were used to detect the same reference material. Runs were performed with 0.1% TFA, 0.1% DFA, 0.02% DFA, 0.01% DFA and 0.1% formic acid mobile phases. Summarized below is the basic procedure that was used across all runs. The results are summarized in FIGS. 3A and 3B.

Reduced IdeS-digested NIST Reference Material 8671 was obtained in the form of the Waters mAb Subunit Standard (Waters, Milford, Mass.). The contents of one vial was reconstituted in water. Analyses of this sample were performed using an LC System sold by Waters Corporation (Milford, Mass.) under the tradename Waters ACQUITY® UPLC® H-Class Bio system with UV and MS detectors sold by Waters Corporation (Milford, Mass.), including a Tunable Ultra-Violet (TUV) Detector and an ACQUITY® QDa® Mass Detector. Method conditions were listed as below. FIGS. 3A and 3B show the comparison of calculated TIC peak height and signal-to-noise ratio of eluted light chain peak using different mobile phase modifiers. The LC conditions are shown in Table 3, the Gradient Conditions are shown in Table 4, and the MS conditions are shown in Table 5.

TABLE 3

| LC Conditions | |
|---|---|
| Column: | Waters BioResolve ™ RP mAb Polyphenyl, 450 Å 2.7 μm, 2.1 × 50 mm |
| Mobile Phase A: | 0.02 to 0.1% (v/v) acid in water |
| Mobile Phase B: | 0.02 to 0.1% (v/v) acid in acetonitrile |
| Column Temperature: | 80° C. |
| Injection Volume: | 2 μL |
| Sample Concentration: | 0.25 μg/μL |
| Sample Diluent: | Water |
| UV Detection: | 280 nm (20 Hz) |

TABLE 4

| Gradient Table | | | | |
|---|---|---|---|---|
| Time (min) | Flow Rate (mL/min) | % A | % B | Curve |
| Initial | 0.300 | 95.0 | 05.0 | Initial |
| 10.00 | 0.300 | 45.0 | 55.0 | 6 |
| 10.50 | 0.300 | 20.0 | 80.0 | 6 |
| 11.50 | 0.300 | 20.0 | 80.0 | 6 |
| 11.51 | 0.300 | 95.0 | 05.0 | 6 |
| 15.00 | 0.300 | 95.0 | 05.0 | 6 |

TABLE 5

MS Conditions

| | |
|---|---|
| Mode: | ESI positive |
| Mass Range: | 350-1250 m/z |
| Collection Mode: | Centroid |
| Cone Voltage: | 15 V |
| Probe Temperature: | 600° C. |
| Capillary Voltage: | 1.5 kV |
| Sample Rate: | 2 pts/s |

Example 3: High Resolution Mass Spectrometry

This example was done to compare the quality of mass spectra produced by commercially available DFA and TFA mobile phases. Runs were performed with 0.1% TFA and 0.1% DFA mobile phases. Summarized below is the basic procedure that was used across all runs. The results are summarized in FIG. 4.

Reduced, IdeS-digested NIST Reference Material 8671 was obtained in the form of the Waters mAb Subunit Standard (Waters, Milford, Mass.). The contents of one vial was reconstituted in water. Analyses of this sample were performed using an LC System sold by Waters Corporation (Milford, Mass.) under the tradename ACQUITY® UPLC® H-Class Bio system with UV and MS detectors sold by Waters Corporation (Milford, Mass.), including a Tunable Ultra-Violet (TUV) Detector and a Synapt® G2-Si QT of MS system for detection. FIGS. 4A and 4B demonstrate the different metal adduct levels in deconvoluted mass spectra using the same concentration of LC-MS grade TFA and reagent grade DFA. The LC conditions are shown in Table 6, the Gradient Conditions for separation with TFA are shown in Table 7, the Gradient Conditions for separation with DFA are shown in Table 8, and the MS conditions are shown in Table 9.

TABLE 6

LC Conditions

| | |
|---|---|
| Column: | Waters BioResolve ™ RP mAb Polyphenyl, 450 Å 2.7 µm, 2.1 × 50 mm |
| Mobile Phase A: | 0.1% (v/v) acid in water |
| Mobile Phase B: | 0.1% (v/v) acid in acetonitrile |
| Column Temperature: | 80° C. |
| Injection Volume: | 4 µL |
| Sample Concentration: | 0.25 µg/µL |
| Sample Diluent: | Water |
| UV Detection: | 280 nm (20 Hz) |

TABLE 7

Gradient Table for Separation with TFA

| Time (min) | Flow Rate (mL/min) | % A | % B | Curve |
|---|---|---|---|---|
| Initial | 0.300 | 75.0 | 25.0 | Initial |
| 10.00 | 0.300 | 55.0 | 45.0 | 6 |
| 10.50 | 0.300 | 20.0 | 80.0 | 6 |
| 11.50 | 0.300 | 20.0 | 80.0 | 6 |
| 11.51 | 0.300 | 75.0 | 25.0 | 6 |
| 15.00 | 0.300 | 75.0 | 25.0 | 6 |

TABLE 8

Gradient Table for Separation with DFA

| Time (min) | Flow Rate (mL/min) | % A | % B | Curve |
|---|---|---|---|---|
| Initial | 0.300 | 85.0 | 15.0 | Initial |
| 10.00 | 0.300 | 65.0 | 35.0 | 6 |
| 10.50 | 0.300 | 20.0 | 80.0 | 6 |
| 11.50 | 0.300 | 20.0 | 80.0 | 6 |
| 11.51 | 0.300 | 85.0 | 15.0 | 6 |
| 15.00 | 0.300 | 85.0 | 15.0 | 6 |

TABLE 9

MS Conditions

| | |
|---|---|
| Mode: | ESI positive |
| Mass Range: | 500-4000 m/z |
| Collection Mode: | Continuum |
| Cone Voltage: | 60 V |
| Source Temperature: | 120° C. |
| Desolvation Temperature: | 450° C. |
| Desolvation Gas: | 600 L/h |
| Capillary Voltage: | 2.75 kV |
| Sample Rate: | 5 pts/s |

Example 4: Analysis of Commercially Available DFA

This example was done to show that commercially available DFA does in fact have high levels of metal impurities by quantifying the amount of metal impurities by inductively coupled plasma mass spectrometry.

The metals contained within a sample of 10 mL of difluoroacetic acid (Oakwood, part number 001231, lot D06N) were quantified by inductively coupled plasma mass spectrometry (ICP-MS). The results of this analysis are provided in FIG. 5, as reported in units of part per billion or ng/g. Individual metal concentrations are reported with an uncertainty of ±50%.

Example 5: Preparing High-Purity DFA

Low metal content high-purity DFA was prepared from the commercially available DFA by distillation with a PFA (copolymer of tetrafluoroethylene and perfluoroalkyl vinylether) acid purification system sold by Savillex Corporation (Eden Prairie, Minn.) under the name DST-1000 Acid Purification System. The distillation apparatus was first readied for use by passing through 500 mL of commercially available DFA. One and two passes of distillation were thereafter performed to obtain increasingly pure forms of DFA. (See FIGS. 6A-6C.)

One of the advantages of this particular system is that the still (e.g., reservoir and condenser) are made from PFA. PFA construction minimizes the contamination potential from extractable compounds.

Acid is added to the unit via a front fill tube which also acts as a gauge to show the amount of acid remaining in the vessel (e.g., still). The large domed PFA condenser operates on the principle of differential temperature between ambient air and the heated solution in the reservoir. There is no need for chilled water baths or re-circulating coolant. Heat is transferred to the reservoir via a silicone rubber heating jacket with an embedded low wattage resistance heating element. The heating jacket has a thermal fuse to disable the heater to protect against overheating. The power setting is adjustable and allows for an operating distillation temperature of 50 to 90 degrees C. Operating temperatures may vary with the liquid volume in the reservoir, and the temperature of the operating environment. When the acid is heated to sub-boiling temperatures, high purity acid vapor is produced, which condenses on the inside of the still, runs down the side walls of the condenser into a collection channel, and flows through a tube into the collection bottle.

Example 6: Low Abundance Variants for ADC Characterization

The technology is applicable to new methods for mAb and ADC (anti-body drug conjugate) subunit analysis. Subunits have been routinely characterized by separations with a sub-2 μm C4-bonded organosilica 300 Å fully porous stationary phase, a separation temperature of 80° C., 0.1% TFA mobile phases, and eluent comprised of 90% acetonitrile and 10% isopropanol, the latter being needed to facilitate the recovery of hydrophobic proteins. A result typical of this method is provided in FIGS. 7A and 7B.

Figures 7A, 7B:
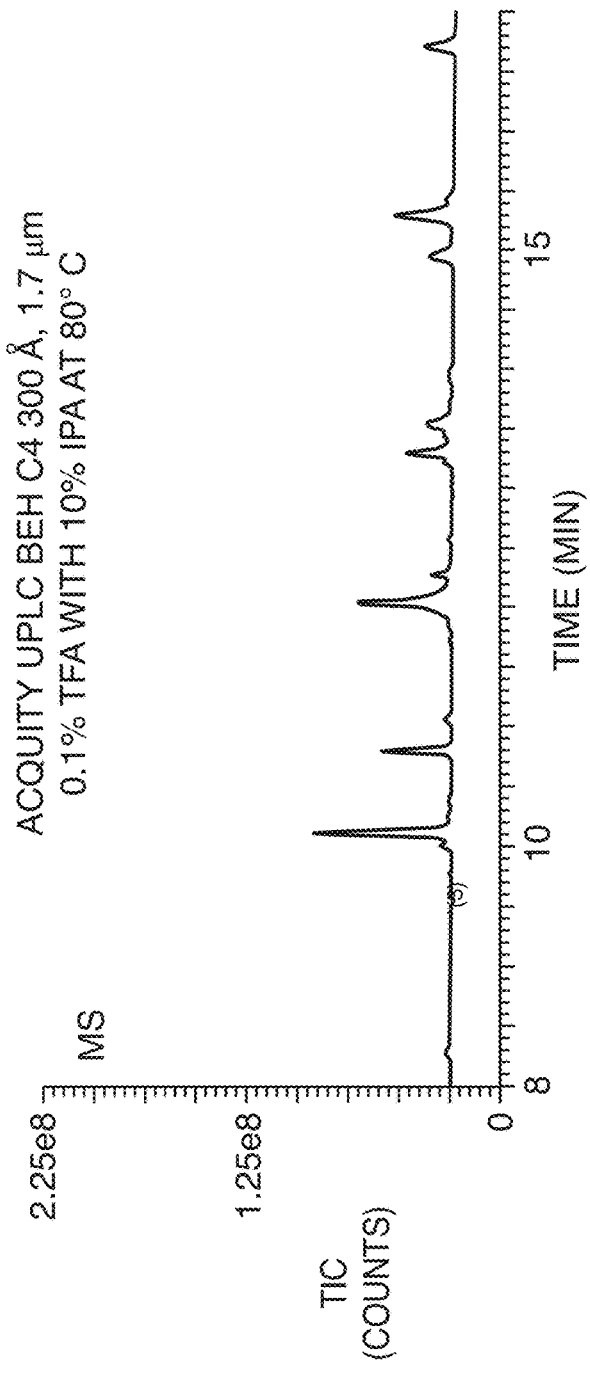
FIG. 7A shows TIC (counts) from a cysteine-linked auristatin conjugated antibody as separated with a C4-bonded organosilica 300 Å fully porous stationary phase, 0.6 mL/min flow rate, 80° C. temperature, 0.1% TFA modified mobile phases and 90:10 CAN/IPA eluent.
FIG. 7B shows total absorption (AU) from a cysteine-linked auristatin conjugated antibody as separated with a C4-bonded organosilica 300 Å fully porous stationary phase, 0.6 mL/min flow rate, 80° C. temperature, 0.1% TFA modified mobile phases and 90:10 CAN/IPA eluent.
Figure 7C:
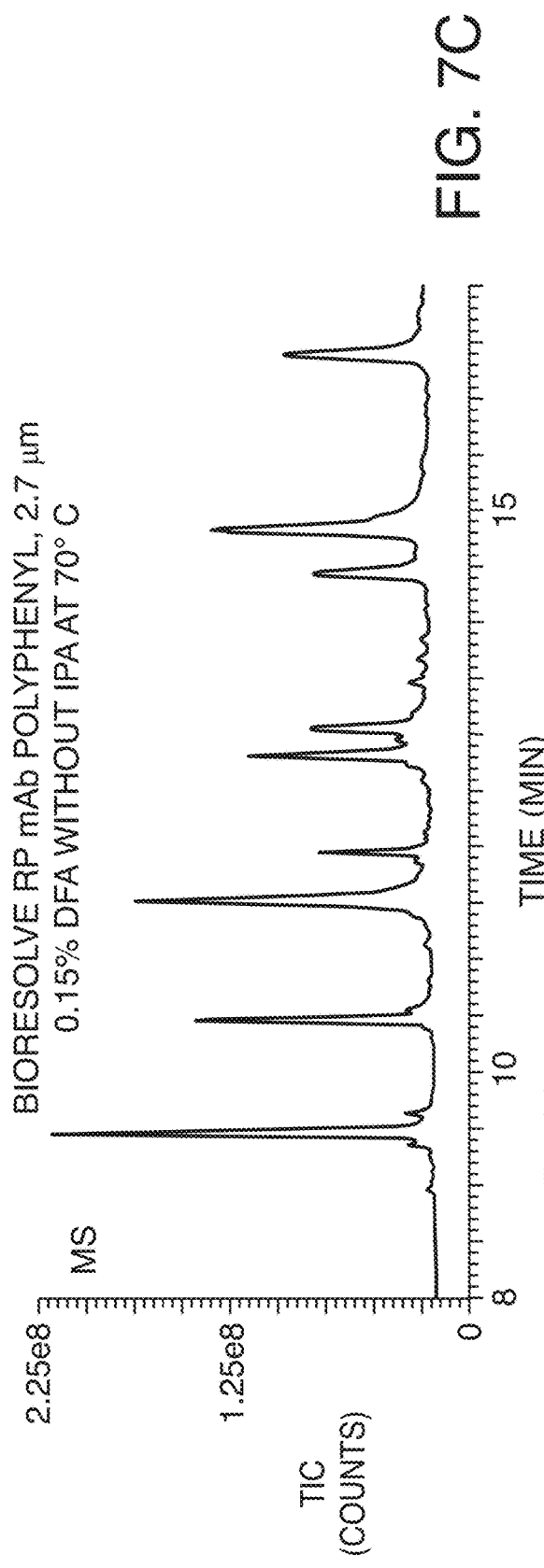
FIG. 7C shows TIC (counts) from a cysteine-linked auristatin conjugated antibody as separated with a new platform method consisting of a phenyl bonded 2.7 µm superficially porous 450 Å stationary phase, 0.6 mL/min flow rate, 70° C. temperature, and 0.15% DFA modified mobile phases, according to an illustrative embodiment of the technology.
Figure 7D:
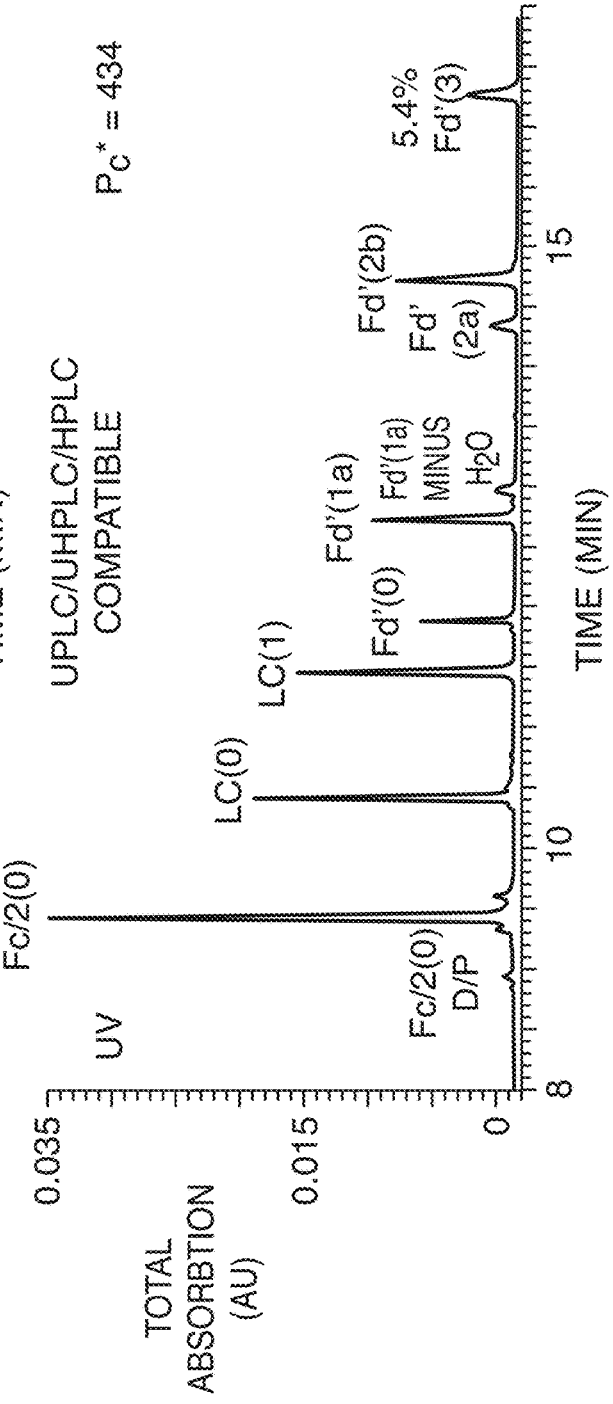
FIG. 7D shows total absorption (AU) from a cysteine-linked auristatin conjugated antibody as separated with a new platform method consisting of a phenyl bonded 2.7 µm superficially porous 450 Å stationary phase, 0.6 mL/min flow rate, 70° C. temperature, and 0.15% DFA modified mobile phases, according to an illustrative embodiment of the technology.
Figure 8C:
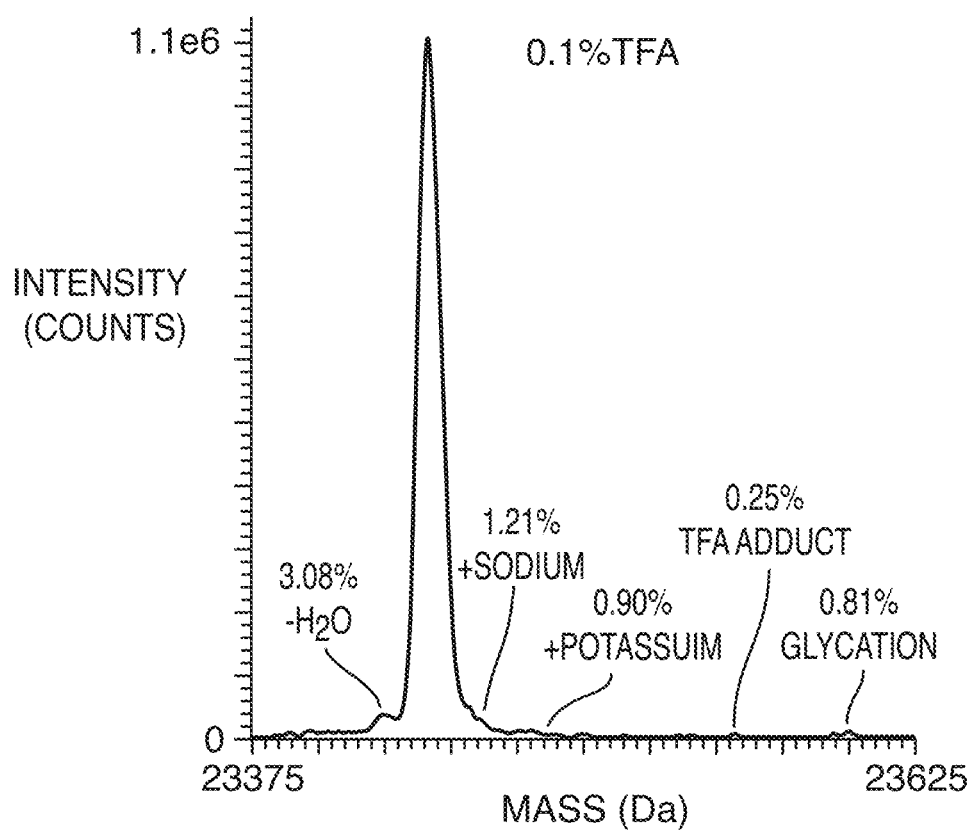
FIG. 8C is a deconvoluted MS spectra of the unmodified LC fragment from the cysteine-linked auristatin ADC obtained using 0.1% MS-grade TFA modified mobile phase, according to an illustrative embodiment of the technology. Separations performed with a BioResolve RP mAb Polyphenyl 450 Å, 2.7 µm, 2.1×150 mm column using a flow rate of 0.6 mL/min, column temperature of 80° C., and 1 µg mass loads.

A new technique was developed that simplified the method of FIGS. 7A and 7B, accelerated turn-around, and/or improved sensitivity. By using a phenyl-bonded superficially porous stationary phase, higher resolution and improved selectivity was gained along with a reduction in backpressure and ability to use faster chromatographic velocities. With this change, it was possible to exclude IPA from the mobile phase without significantly affecting peak capacity or protein recovery. Along with the adoption of DFA, it was also possible to reduce the separation temperature. This new method is exemplified in FIGS. 7C and 7D. It is of note that, while the sub 2 μm column required ultrahigh pressure instrumentation, the 2.7 μm based approach could be transferable to other less specialized instrumentation by way of having lower operational back pressures. Furthermore, using the latter platform, it was possible to optimize nearly all facets of the chromatographic separation and to facilitate some more strenuous examples of deep-level characterization. Two examples of low abundance variants are discoverable within the shoulder peaks adjacent to the unmodified Fc/2 subunit (See FIGS. 7A-7D). Mass spectra corresponding to these species are displayed in FIGS. 8A-8C.

The DFA method (FIG. 8B) produced higher signal-to-noise spectra, which could be used to more confidently confirm +16 Da (pre-peak) and +674 Da (post-peak) mass shifts and the corresponding identification of Fc domain oxidation and an aglycosylated isoform.

Example 7: Modifier Preparation, Small Molecule Analyte Preparation, and Chromatographic Setup The technology is applicable small molecule analysis. Mobile phases were prepared by adding either highly-purified DFA (Waters Corp, and distilled as discussed in Example 5), formic acid Optima LC-MS grade (Fisher Chemical, P/N A117-50) or TFA Optima LC-MS grade (Fisher Chemical, P/N A116-50) at 0.1% (v/v) to both aqueous and acetonitrile mobile phases. The small molecule analytes at 2.5 μg/mL concentration in water and their corresponding optimized multiple reaction monitoring (MRM) transitions (2,6-dimethylaniline (m/z 121.9→104.6), toluidine (m/z 108.0→90.6), 4-chloro-N-methylaniline (m/z 142.1→107.1), histidine (m/z 156.0→110.1), 2-chloro-4-nitroaniline (m/z 173.0→126.0), thiamine (m/z 265.1→121.9) and tryptophan (m/z 205.1→146.0) in positive ESI mode and histidine (m/z 154.0→92.9), guanosine-5'-monophosphate (GSMP) (m/z 321.9→104.6), thymidine-5'-monophosphate (TSMP) (m/z 321.9→104.6) and niflumic acid (m/z 281.1→237.2) in negative ESI mode) were analyzed by separating them on a Waters ACQUITY BEH C18, 1.7 μm, 2.1×50 mm column using a UHPLC system (commercially available from Waters Technologies Corporation, ACQUITY I-Class UPLC system with a Xevo-TQS MS/MS). That is, basic small molecules were prepared for positive-ESI ionization mode analysis and acidic/amphoteric small molecules were prepared for negative-ESI ionization mode analysis.

Figure 9A:
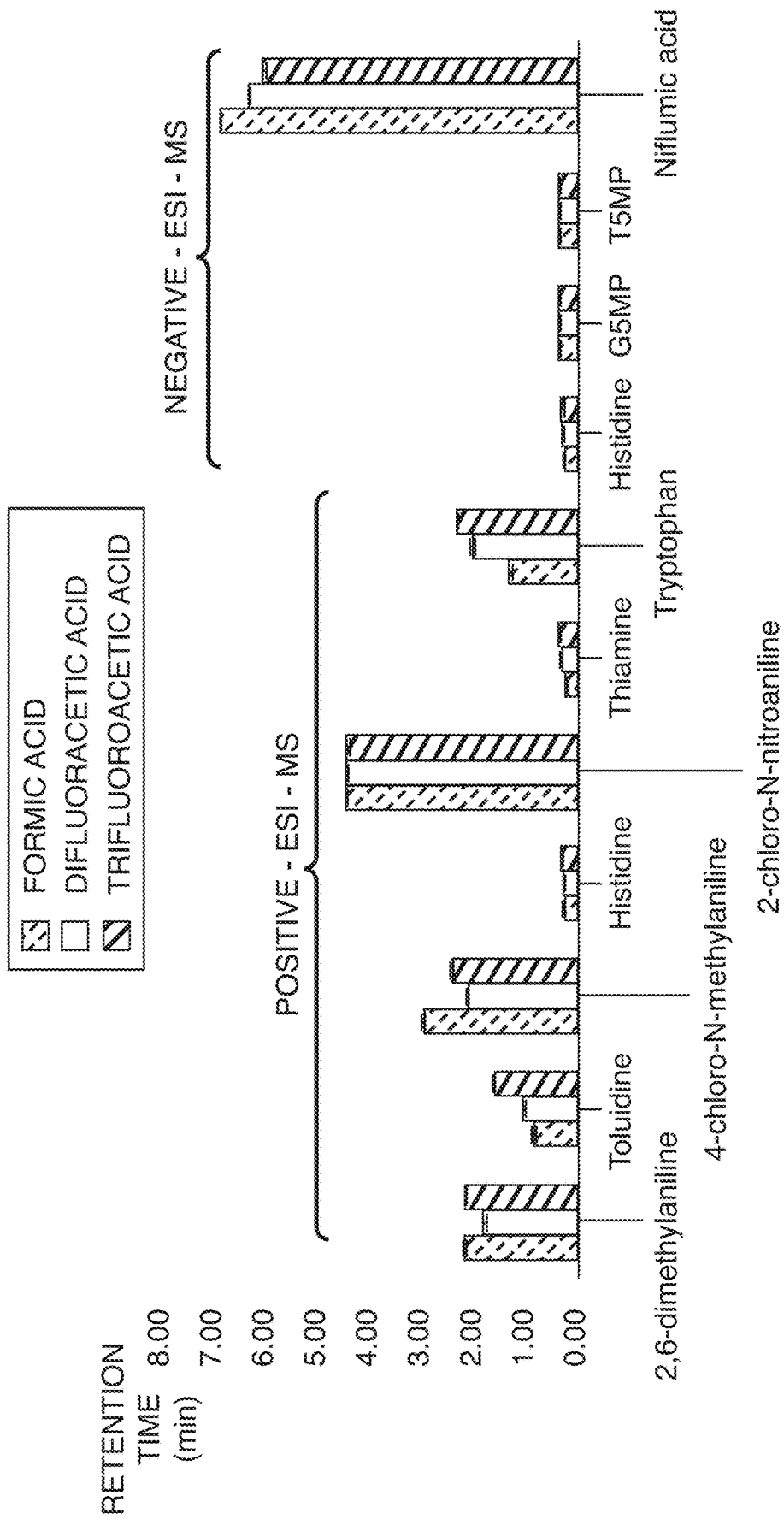
FIG. 9A is a graph providing a retention time comparison for various small molecule analytes using additives 0.1% (v/v) formic acid (left bar chart); 0.1% (v/v) highly-purified DFA (center bar chart); and 0.1% (v/v) TFA (right bar chart) in both the aqueous and organic mobile phases with a Waters ACQUITY BEH C18, 1.7 micron, 2.1×50 mm column. The error bars show one standard deviation for triplicate measurements.

Example 8: Retention Time and Peak Width Comparison for Small Molecule Analytes Using Different Modifiers Chromatographic retention and peak width were measured under acetonitrile gradient conditions (5-100%). FIG. 9A shows a comparison of the retention times for all the analytes using the three mobile phase modifiers prepared as described in Example 7. For each small molecule analyte the results of retention time are provided in bar graph form with formic acid modifier appearing as the left most bar, DFA modifier appearing as the center bar, and TFA modifier appearing as the right most bar. While the retention times of the neutral analyte 2-chloro-4-nitroaniline were similar for the three modifiers, the retention times of the other compounds, which are ionized, showed significant differences. The aqueous modifier solutions vary in pH from 2.0 (0.1% v/v TFA and 0.1% DFA) to 2.7 (0.1% v/v formic acid), and this affects the retention times of analytes that have $pK_a$ values in the 1-4 range. For the compounds that have a positive charge under the separation conditions, differences in the hydrophobicity of the modifiers also affect the retention times because the anion of the modifier ion-pairs with positively-charged analytes. TFA has the greatest hydrophobicity and formic acid the least.

Figure 9B:
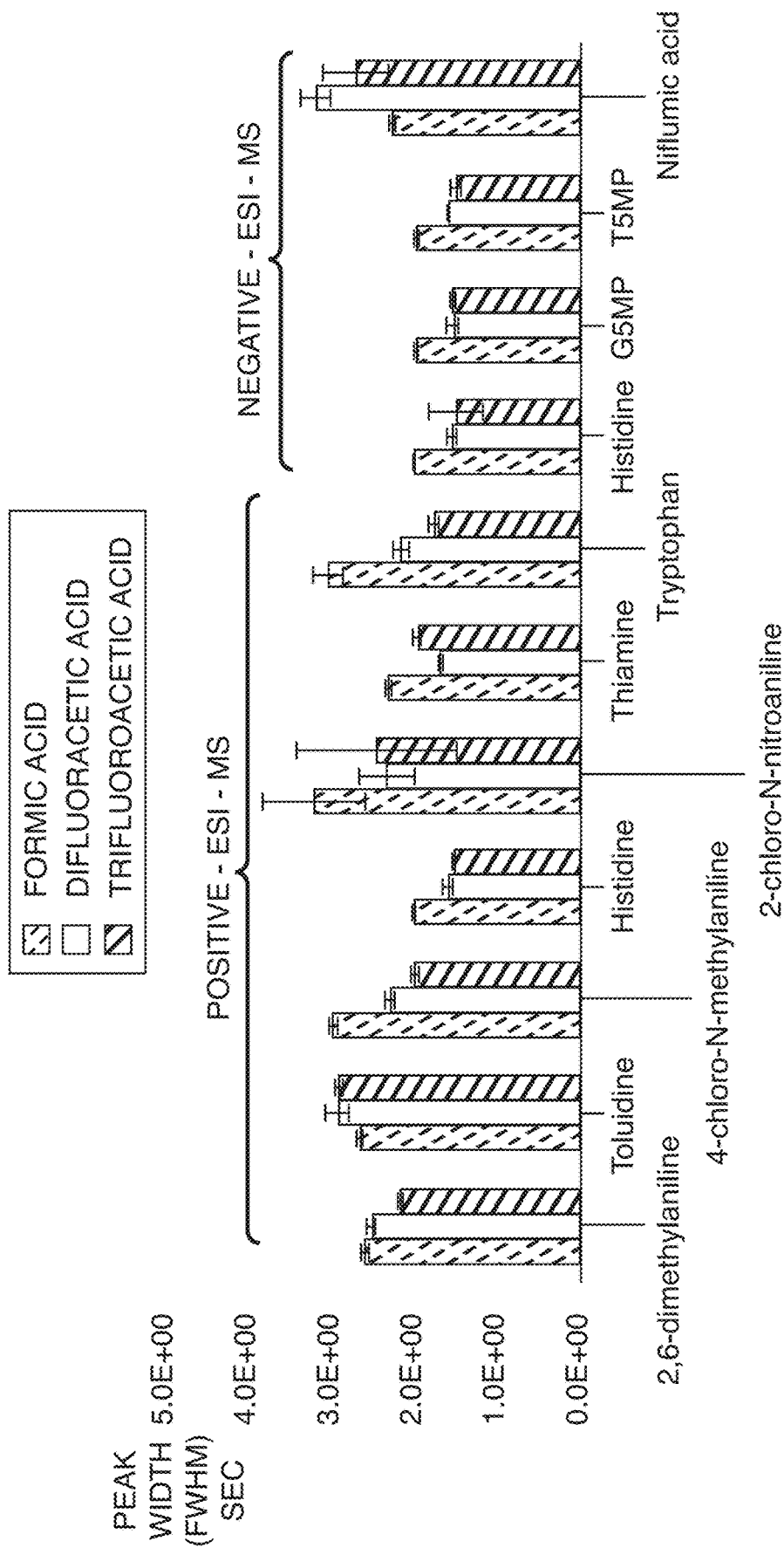
FIG. 9B is a graph providing a chromatographic peak comparison (full width at half max height) for various small molecule analytes using additives 0.1% (v/v) formic acid (left bar chart); 0.1% (v/v) highly-purified DFA (center bar chart); and 0.1% (v/v) TFA (right bar chart) in both the aqueous and organic mobile phases with a Waters ACQUITY BEH C18, 1.7 micron, 2.1×50 mm column. The error bars show one standard deviation for triplicate measurements.

FIG. 9B shows a comparison of the chromatographic peak widths for all the analytes using the three mobile phase modifiers. For each small molecule analyte the results of peak width are provided in bar graph form with formic acid modifier appearing as the left most bar, DFA modifier appearing as the center bar, and TFA modifier appearing as the right most bar. For most of the compounds, the peak widths obtained using DFA are smaller than those obtained using formic acid and similar to those obtained using TFA.

Example 9: MS Signal Response Comparison for Small Molecule Analytes Using Different Modifiers and at Different Aqueous/Organic Ratios MS signal response for the small molecule analytes and three different modifiers prepared in Example 7 were measured under acetonitrile gradient conditions (5-100%). Since the aqueous/organic ratio in the mobile phase can impact the MS signal response, two probe analytes, 2,6-dimethylaniline and 4-chloro-N-methylaniline were also analyzed by MS, post LC infusion at different aqueous/organic ratios to compare the MS signal response obtained using the three additives at fixed aqueous/organic compositions.

Figure 10A:
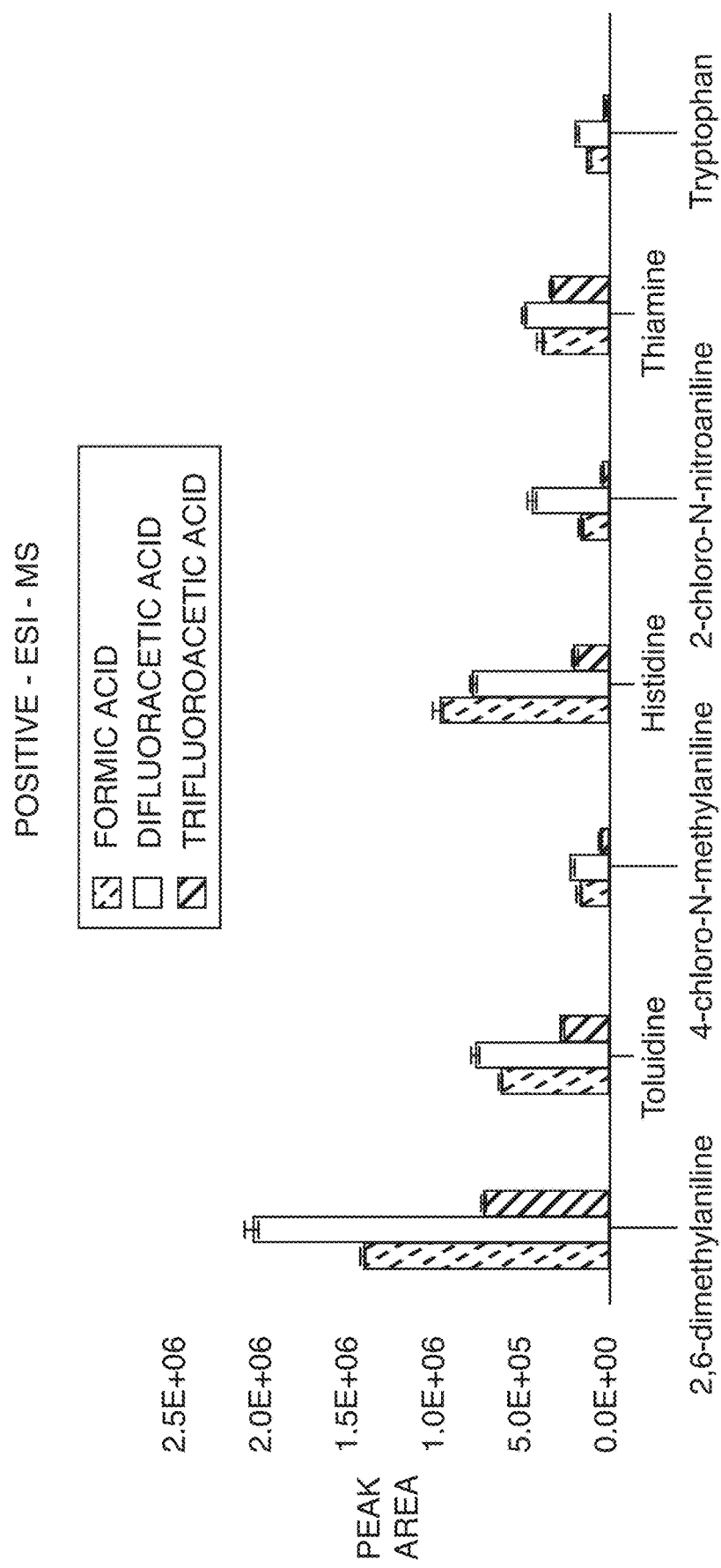
FIG. 10 A is a graph providing MS signal response comparison for various basic small molecule analytes using additives 0.1% (v/v) formic acid (left bar chart); 0.1% (v/v) highly-purified DFA (center bar chart); and 0.1% (v/v) TFA (right bar chart) in both the aqueous and organic mobile phases under ESI positive ionization mode. The error bars show one standard deviation for triplicate measurements.
Figure 10B:
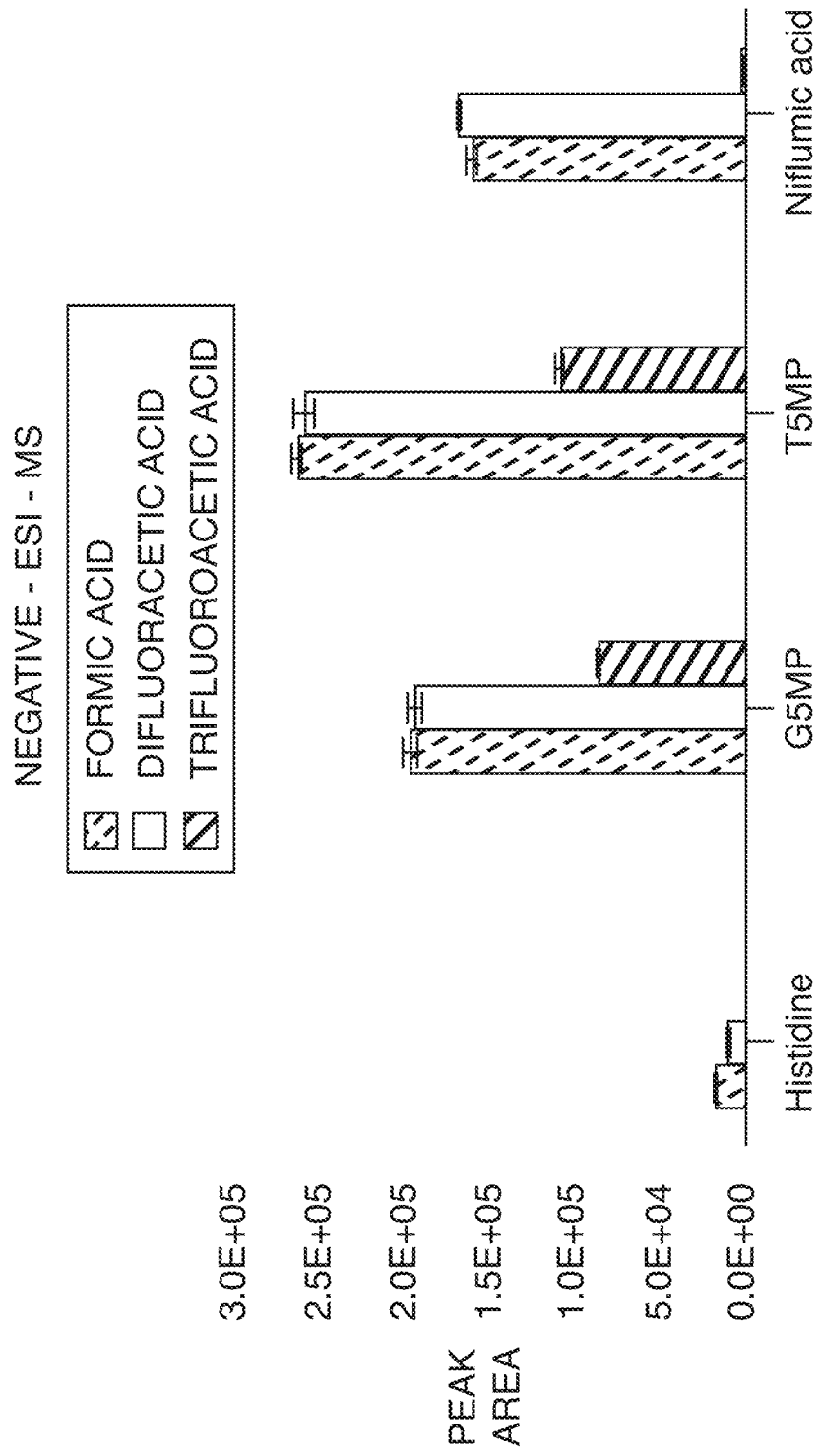

FIGS. 10A and 10B show the MS signal response (peak area) for all the analytes under the same LC-MS conditions using the three mobile phase modifiers. Once again, formic acid results are shown as the left-most bar, DFA are shown as the center bar, and TFA is shown as the right most bar for each small molecule analyte. For all the analytes, MS signal response using DFA was significantly higher (up to two-fold in magnitude) when compared to TFA. For acidic analytes (e.g., FIG. 10B) the MS signal response when using DFA was comparable to the response using formic acid. Most of the basic analytes showed improved MS signal response using DFA compared to formic acid (e.g., FIG. 10A).

Figure 11A:
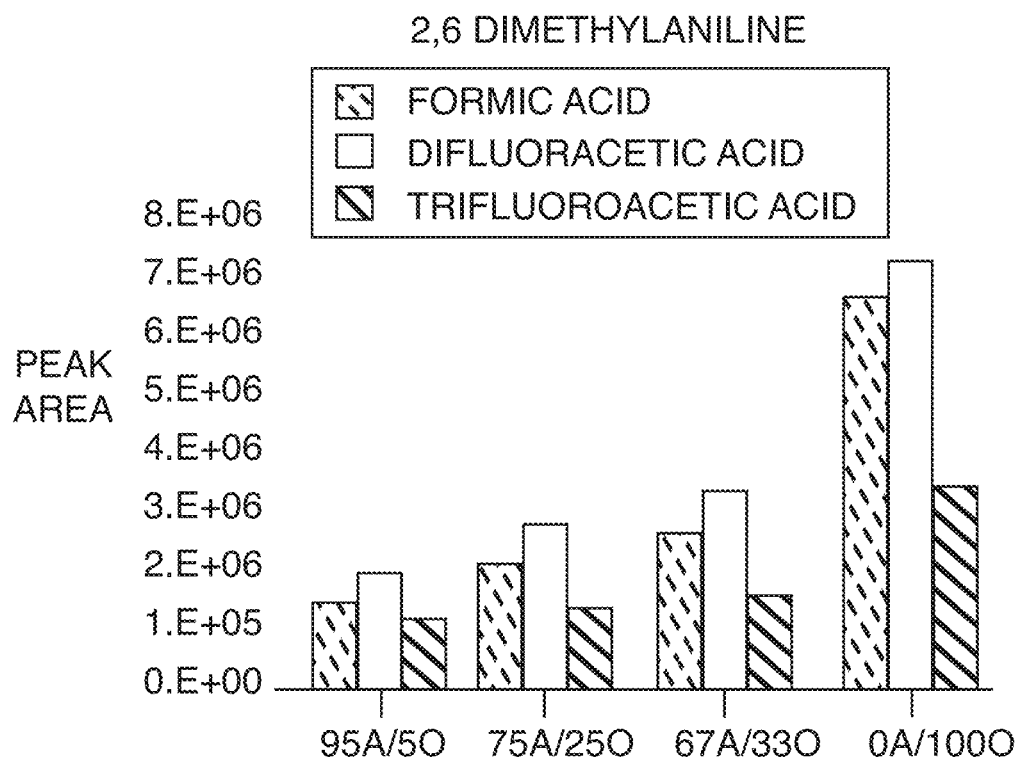
FIG. 11 A is a graph providing MS signal response comparison at different aqueous/organic ratios for basic small molecule (2,6-dimethylaniline) using additives 0.1% (v/v) formic acid (left bar chart); 0.1% (v/v) highly-purified DFA (center bar chart); and 0.1% (v/v) TFA (right bar chart) in both the aqueous and organic mobile phases under ESI positive ionization mode.
Figure 11B:
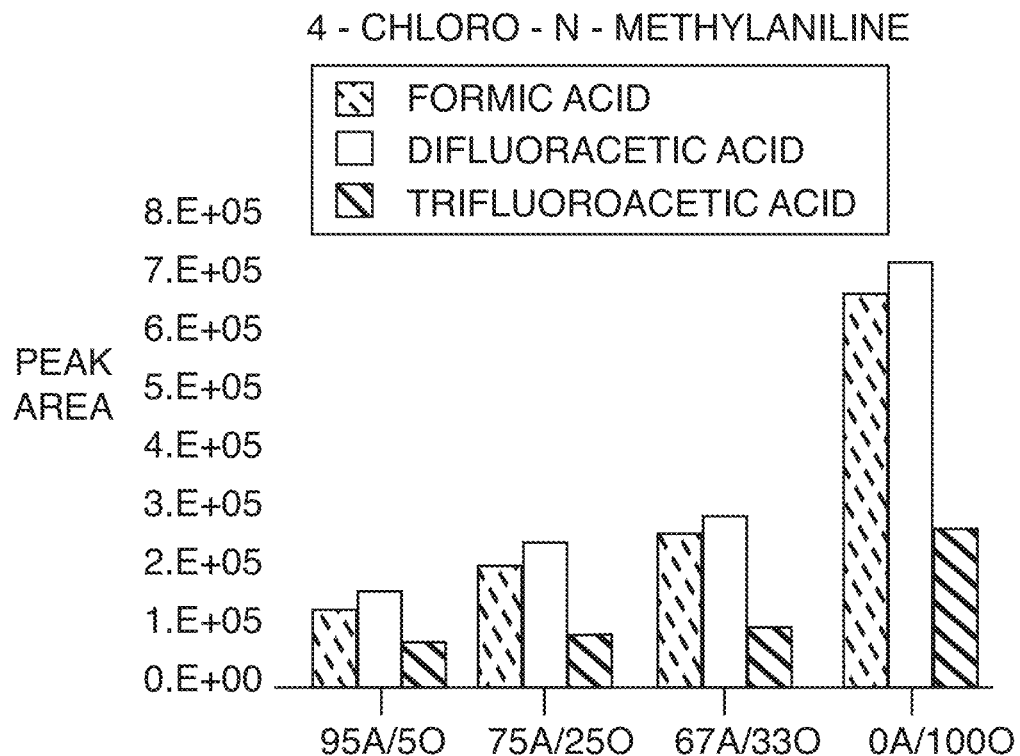

FIGS. 11A and 11B show the MS signal response for two of the basic analytes, 2,6-dimethylaniline (FIG. 11A) and 4-chloro-N-methylaniline (FIG. 11B) at fixed aqueous/organic mobile phase compositions. Formic acid results are presented as the left most bar, DFA results are presented as the center bar, and TFA results are presented as the right most bar for each ratio presented on the horizontal axis. It is evident from the results that the MS signal response for these analytes is slightly higher using DFA as purified according to Example 5, compared to formic acid and is significantly higher when compared to TFA at different aqueous/organic mobile phase compositions.

CONCLUSIONS

The increasing complexity of biopharmaceutical modalities requires there be improvements made in analytical methodologies. Reversed-phase liquid chromatography is a powerful technique for the separation of proteins and/or peptides at all molecular levels, and it becomes inordinately more powerful when coupled to mass spectrometry. However, depending on the use of conventional acid modifiers, such as trifluoroacetic acid (TFA) and formic acid (FA), protein and/or peptide RPLC often exhibits excellent chromatographic resolution at the compromise of MS sensitivity or, vice versa, excellent MS sensitivity at the compromise of separation quality. The technology described herein, demonstrates a new choice for LC-MS analyses based on the use of highly purified difluoroacetic acid (DFA) with or without a high-coverage phenyl-bonded superficially porous stationary phase. The use of phenyl-bonded superficially porous stationary phases builds upon the advantages of superficially porous particles with a unique phenyl bonding that aids in reducing temperature and ion pairing dependence. This lends itself well to the use of DFA for protein and/or peptide separations, wherein it has now been shown that this alternative ion pairing modifier can reach an optimization between chromatography and mass spectrometry otherwise unreachable by TFA and FA.

Purified DFA proved to be key to finding a step change in protein and/or peptide LC-MS capabilities. As used with the aforementioned high-coverage phenyl stationary phase, a DFA-based method greatly improved subunit-level profiling of a very hydrophobic, cysteine-linked auristatin conjugated ADC (see, e.g., Example 6). Moreover, in addition to providing benefits to chromatographic resolution and MS sensitivity, this robust platform was found to greatly increase protein recovery without the need to use alcohol co-solvents for elution, even with a reduction in column temperature. This is theorized to be an effect resulting from purified DFA being sufficiently acidic so as to minimize ionic secondary interactions (unlike FA) but not as hydrophobic as TFA to force excessively strong adsorption.

In addition to biomolecule LC-MS studies, the present technology proved to provide improved results for small molecule LC-MS studies. In particular, the highly-purified DFA described herein provided a modifier with low impurities/contaminates for MS analysis of small molecules. DFA purified in accordance with the present technology shows great potential for use as a mobile phase modifier in small molecule LC-MS analysis, adding a new choice to the limited number of suitable acidic modifiers available for small molecule LC-MS analysis. For the analytes tested, DFA exhibits the combined benefits of formic acid and TFA modifiers, giving narrow peak widths comparable to those obtained using TFA and high MS signal responses similar to those obtained using formic acid (or in some cases even higher responses than that with formic acid).

While this disclosure has been particularly shown and described with reference to example embodiments thereof, it will be understood by those skilled in the art that various changes in form and details may be made therein without departing from the scope of the technology encompassed by the appended claims.

What is claimed is:

1. A method of separating at least one small molecule from a sample, the method comprising:
   flowing a mobile phase through a chromatography column wherein the mobile phase comprises about 0.005% (v/v) to about 2.50% (v/v) difluoroacetic acid and less than about 100 ppb of any individual impurity;
   injecting the sample containing the at least one small molecule into the mobile phase; and separating the at least one small molecule from the sample.

2. The method of claim 1, wherein the chromatography column is a liquid chromatography column.

3. The method of claim 1, wherein the chromatography column is a HILIC chromatography column.

4. The method of claim 1, wherein the chromatography column is a mixed mode chromatography column.

5. The method of claim 1, wherein the chromatography column further comprises a stationary phase having a polymeric polystyrene divinyl benzene surface chemistry.

6. The method of claim 1, wherein the mobile phase comprises less than about 50 ppb of any individual impurity.

7. The method of claim 1, wherein the mobile phase comprises less than about 20 ppb of any individual impurity.

8. The method of claim 1, wherein the mobile phase comprises about 0.01% to about 0.9% difluoroacetic acid.

9. The method of claim 1, further comprising detecting the at least one small molecule with a mass spectrometer.

10. The method of claim 9, further comprising generating small molecule ions from the separated at least one small molecule.

11. The method of claim 10, wherein the small molecule ions are generated by electrospray ionization.

12. The method of claim 10, further comprising acquiring a mass spectrum of the small molecule ions.

13. The method of claim 1, wherein the mobile phase further comprises water, acetonitrile, methanol, propanol, butanol, pentanol, or combinations thereof.

* * * * *